(12) United States Patent
Kung et al.

(10) Patent No.: US 10,007,164 B2
(45) Date of Patent: Jun. 26, 2018

(54) ORGANIC COMPOUNDS, LIGHT MODULATING COMPOSITION AND LIGHT MODULATING DEVICES EMPLOYING THE SAME

(71) Applicant: INDUSTRIAL TECHNOLOGY RESEARCH INSTITUTE, Hsinchu (TW)

(72) Inventors: Yu-Ruei Kung, New Taipei (TW); Li-Ting Huang, New Taipei (TW); Chyi-Ming Leu, Jhudong Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days. days.

(21) Appl. No.: 14/978,906

(22) Filed: Dec. 22, 2015

(65) Prior Publication Data
US 2017/0146881 A1    May 25, 2017

(30) Foreign Application Priority Data
Nov. 20, 2015    (TW) .............................. 104138432 A

(51) Int. Cl.
*C07C 233/43* (2006.01)
*C07C 233/62* (2006.01)
(Continued)

(52) U.S. Cl.
CPC ............ *G02F 1/153* (2013.01); *C07C 233/43* (2013.01); *C07C 233/62* (2013.01);
(Continued)

(58) Field of Classification Search
USPC ....................................................... 548/545
See application file for complete search history.

(56) References Cited

U.S. PATENT DOCUMENTS
7,894,118 B2    2/2011    Hirano et al.

FOREIGN PATENT DOCUMENTS
CN    101903345 A    12/2010
CN    102675636 A    9/2012
(Continued)

OTHER PUBLICATIONS
Shoji, 1988, caplus an 1988:13851.*
(Continued)

*Primary Examiner* — Sun Jae Yoo
(74) *Attorney, Agent, or Firm* — Birch, Stewart, Kolasch & Birch, LLP

(57) ABSTRACT

An organic compound, a light modulating composition and a light modulating device are provided. The organic compound has a chemical structure represented by formula (I):

X—Ar—X    (I)

wherein X is

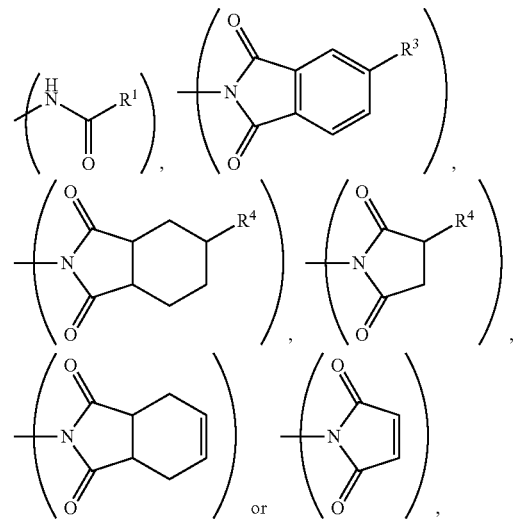

Ar is

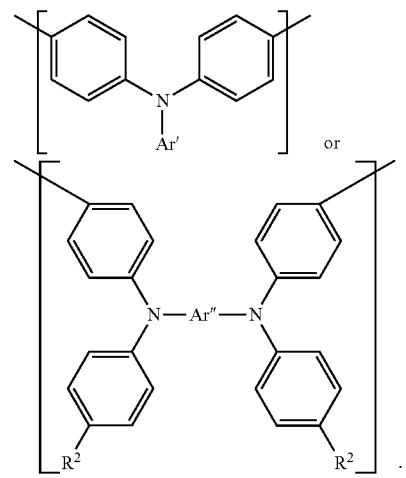

The organic compound is transparent in its neutral state. The amide group or imide group introduced into the aromatic amine not only enhances the solubility of the organic compound in the solvent, but also enhances the electrochemical stability of the organic compound.

20 Claims, 8 Drawing Sheets

(51) Int. Cl.
    *C07D 209/50*    (2006.01)
    *G02F 1/153*     (2006.01)
    *C09K 9/02*      (2006.01)
    *G02F 1/15*      (2006.01)

(52) U.S. Cl.
    CPC ............. *C07D 209/50* (2013.01); *C09K 9/02* (2013.01); *C07C 2101/14* (2013.01); *C09K 2211/1007* (2013.01); *C09K 2211/1014* (2013.01); *C09K 2211/1025* (2013.01); *C09K 2211/1029* (2013.01); *G02F 2001/1502* (2013.01); *G02F 2001/1515* (2013.01)

(56) References Cited

FOREIGN PATENT DOCUMENTS

| CN | 104072474 A  | 10/2014 |
|----|--------------|---------|
| CN | 101768103 A  | 8/2015  |
| JP | 62-126154 A  | 6/1987  |
| JP | 2-306960 A   | 12/1990 |
| JP | 5-34743 A    | 2/1993  |
| JP | 2009-217054 A| 9/2009  |
| JP | 2015-132778 A| 7/2015  |
| TW | 373126       | 11/1999 |
| TW | 200909427 A  | 3/2009  |

OTHER PUBLICATIONS

Cospito et al., Materials Chemistry and Physics, 2013, 431-434.*
Cospito et al., abstract, 2013, caplus an 2013:730736.*
Kudo et al., 1991, caplus an 1991:247955.*
Kung et al., 2011, caplus an 2011:413370.*
Funyuu et al., 2015, caplus an 2015:1363911.*
Taiwanese Office Action and Search Report, dated May 24, 2016, for corresponding Taiwanese Application No. 104138432.
Hsiao et al., "Novel Aromatic Polyamides and Polyimides Functionalized with 4-tert-Butyltriphenylamine Groups", Journal of Polymer Science: Part A: Polymer Chemistry, vol. 44, 2006, pp. 4579-4592.
Wang et al., "Substituent Effects on Electrochemical and Electrochromic Properties of Aromatic Polyimides with 4-(Carbazol-9-yl)triphenylamine Moieties", Journal of Polymer Science, Part A: Polymer Chemistry, vol. 52, 2014, pp. 1172-1184.
Wang et al., "Synthesis, optical and electrochemical properties of new hyperbranched poly(triphenylamine amide)s", Polymer, vol. 49, 2008, pp. 4087-4093.
Yen et al., "Enhanced near-infrared electrochromism in triphenylamine-based aramids bearing phenothiazine redox centers", Journal of Materials Chemistry, vol. 20, 2010, pp. 9886-9894.
Yen et al., "Synthesis and Unexpected Electrochemical Behavior of the Triphenylamine-Based Aramids with Ortho- and Para-Trimethyl-Protective Substituents", Journal of Polymer Science: Part A: Polymer Chemistry, vol. 48, 2010, pp. 5271-5281.
Yen et al., "Transmissive to black electrochromic aramids with high near-infrared and multicolor electrochromism based on electroactive tetraphenylbenzidine units", J. Mater. Chem., vol. 21, 2011, pp. 6230-6237.
Zhang et al., "The preparation and electrochromic properties of the polyurethanes containing triphenylamine moiety", Journal of Electroanalytical Chemistry, vol. 717-718, 2014, pp. 165-171.
De Simone, B.C., et al, "Theoretical and experimental investigation on the near-infrared and UV-vis spectral regions of a newly syntheized triarylamine electronchromic system," Theor. Chem. Acc., 2012, vol. 131, No. 5, pp. 1-9.
Japanese Office Action for Appl. No. 2015-256675 dated Jun. 6, 2017 (w/ English translation).
Jung, C., et al, "Synthesis of polymide possessing NLO chromophore and properties of Langmuir-Blodgett films," Journal of Photopolymer Science and Technology, 1998, vol. 11, No. 2, pp. 211-216.
Wu, J.H., et al, "High-efficiency flourescent polyimides based on locally excited triarylamine-containing dianhydride moieties," Polymer Chemistry, 2015, vol. 6, pp. 5225-5232.
Zhang, X., et al, "Multi-Maleimides Bearing Electron-Donating Chromophores: Reversible Fluorescence and Aggregation Behavior," J. Am. Chem. Soc., 2004, vol. 126, pp. 12200-12201.
Chinese Office Action dated Feb. 24, 2018 for corresponding application No. 201511022262.9.
Kung et al., "New Polyimides incorporated with diphenylpyrenylamine unit as fluorophore and redox-chromophore", Journal of Polymer Science Part A: Polymer Chemistry, Mar. 24, 2011, vol. 49, Issue 8, pp. 2210-2221.
Wang et al., "High Tg donor-embedded polyimides for second-order nonlinear optical applications", Elsevier, Polymer 41, 2000, pp. 2583-2590.

* cited by examiner

ORGANIC COMPOUNDS, LIGHT MODULATING COMPOSITION AND LIGHT MODULATING DEVICES EMPLOYING THE SAME

CROSS REFERENCE TO RELATED APPLICATIONS

This Application claims priority of Taiwan Patent Application No. 104138432, filed on Nov. 20, 2015, the entirety of which is incorporated by reference herein.

TECHNICAL FIELD

The present disclosure relates to organic compounds, light modulating compositions, and light modulating devices employing the same.

BACKGROUND

Light modulating devices are attractive in green energy industries due to their low driving voltage and bistability. Recently, the major part of light modulating material is inorganic oxides for longer lifetime and endurance, however, films thereof are prepared by using expensive processes and equipment such as vacuum deposition, spray pyrolysis, or sputtering. Even ignoring the cost of processing, the inorganic oxide still has shortcomings such as a slow electrochromic rate, less color variation, and the like. In an organic system, light modulating organic materials use conjugated polymer with more color variation and fast electrochromic rates. However, the conjugated compound has shortcomings such as expensive monomers, complicated synthesis, and formation by electro-polymerization. The electrochromic conjugated polymer has an appearance of deep color due to its conjugated length. Although the deep color can be lightened by applying a voltage, the conjugated polymer cannot be fully transparent. In other words, the conjugated polymer must be electrified to effect a transparent state, thereby leading to the problem of high energy consumption.

Accordingly, there is a need for a novel electrochromic organic material to meet the requirements of transparency, film-firming ability, and electrochromicity.

SUMMARY

The present disclosure relates to organic compounds, light modulating compositions, and light modulating devices employing the same.

In accordance with one embodiment of the disclosure, an organic compound is provided. The organic compound has a chemical structure represented by formula (I):

X—Ar—X   (I)

wherein X is

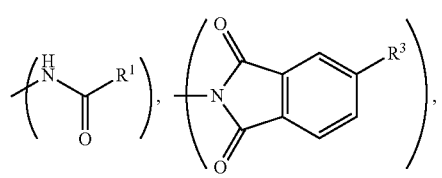

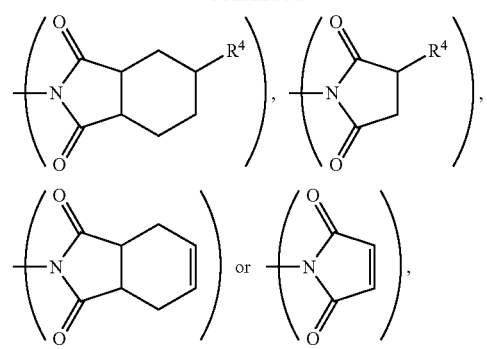

$R^1$ is an alkyl, $R^3$ is H, an alkyl, or an alkoxy, $R^4$ is H, or methyl; Ar is

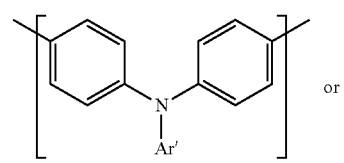

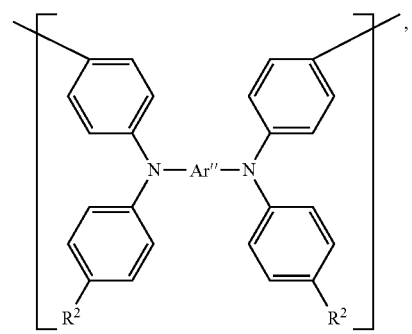

Ar' is

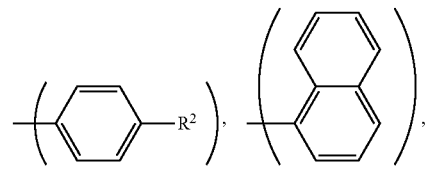

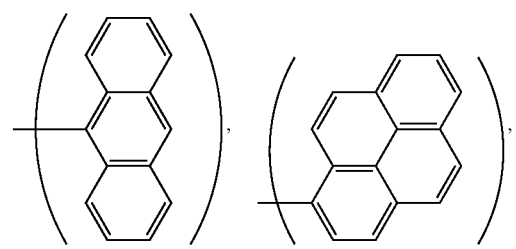

-continued

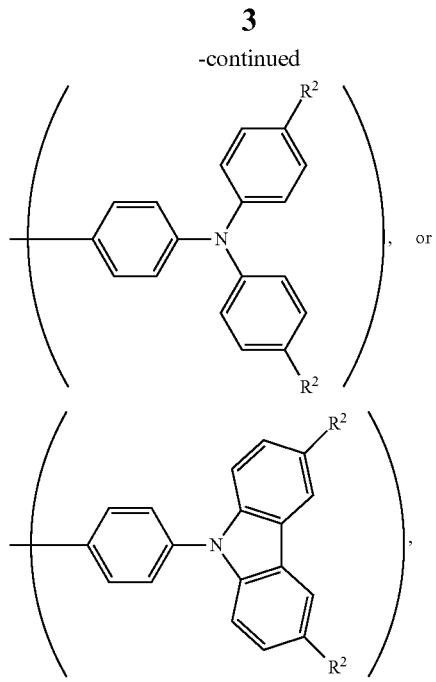, or

Ar" is

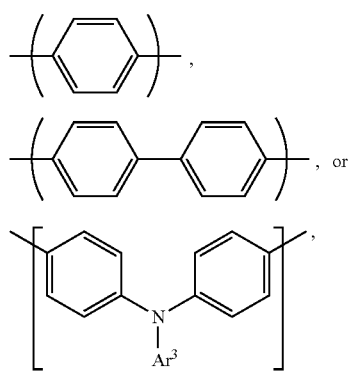, or

Ar³ is

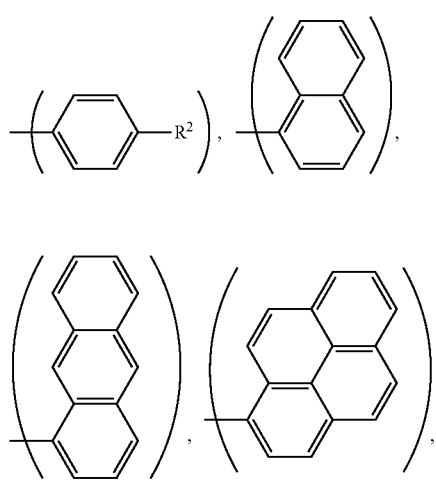

-continued

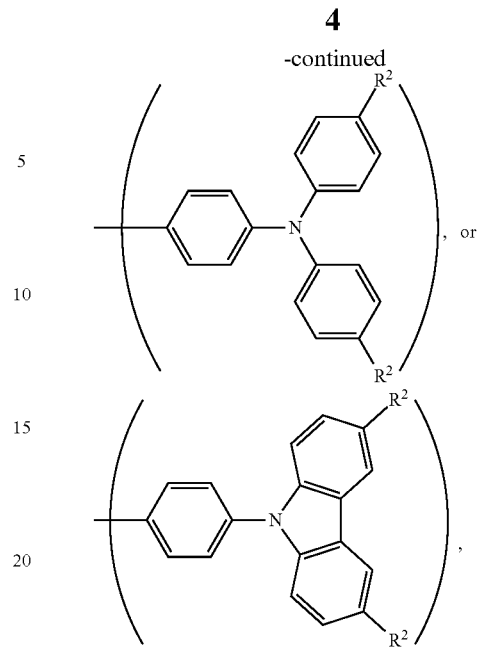, or and R² is H, an alkyl, or an alkoxy.

In accordance with another embodiment of the disclosure, a light modulating composition is provided. The composition includes a first oxidizable compound, a reducible compound, an electrolyte and a solvent, wherein the first oxidizable compound includes the aforementioned organic compound.

In accordance with another embodiment of the disclosure, a light modulating device is provided. The light modulating device includes a pair of electrodes, an isolating unit and a light modulating composition. The pair of electrodes includes a first transparent substrate with a first transparent conductive layer on a surface of the transparent substrate and a second transparent substrate with a second transparent conductive layer on a surface of the transparent substrate. The pair of electrodes is disposed by arranging the first transparent conductive layer and the second transparent conductive layer to face each other. The isolating unit inserted between the first and second transparent conductive layers to form a cell. Then, the light modulating composition is filled in the cell. The composition includes a first oxidizable compound, a reducible compound, an electrolyte and a solvent. The first oxidizable compound includes the aforementioned organic compounds.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
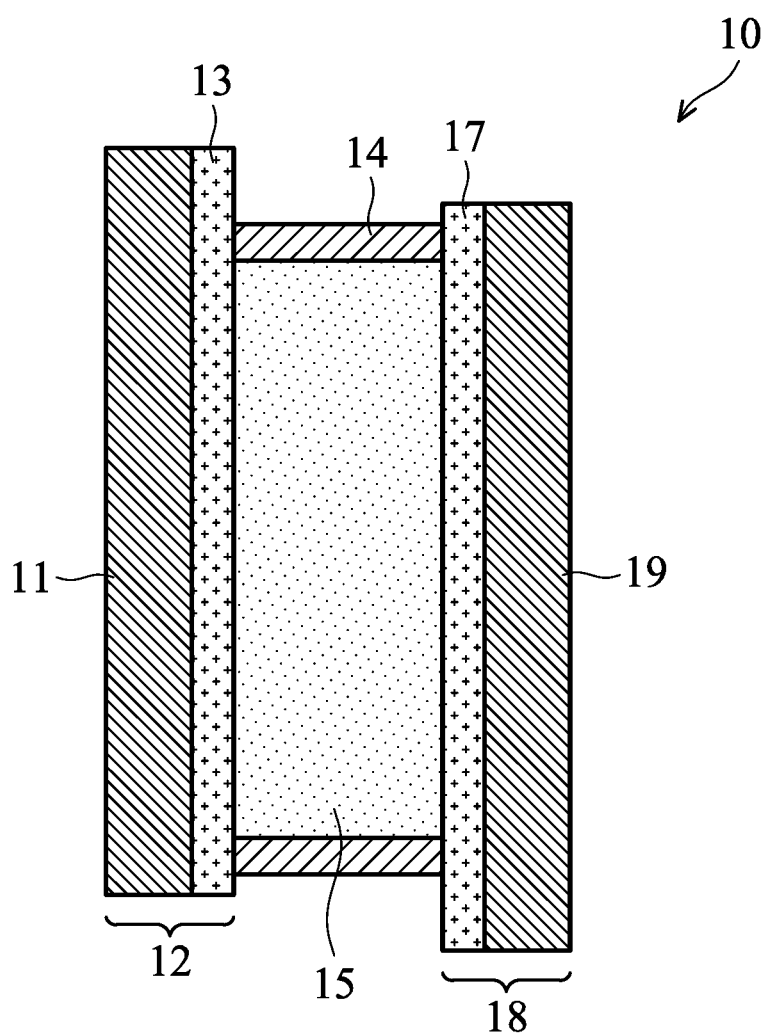
FIG. 1 shows a light modulating device in one embodiment of the disclosure.

In accordance with some embodiments of the disclosure, an organic compound is provided. The organic compound has a chemical structure represented by formula (I):

$$X—Ar—X \qquad (I)$$

wherein X can be

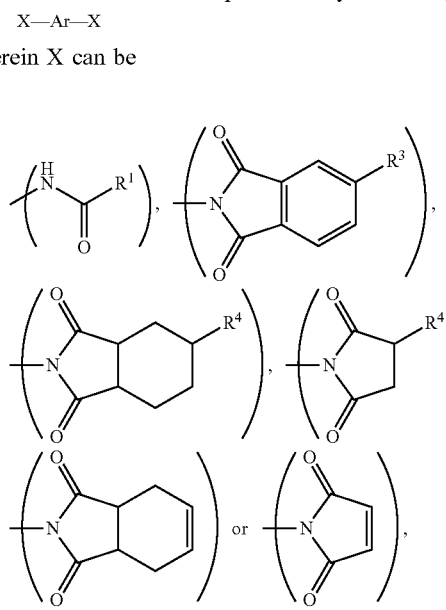

$R^1$ can be an alkyl, $R^3$ can be H, an alkyl, or an alkoxy, $R^4$ can be H, or methyl; Ar can be

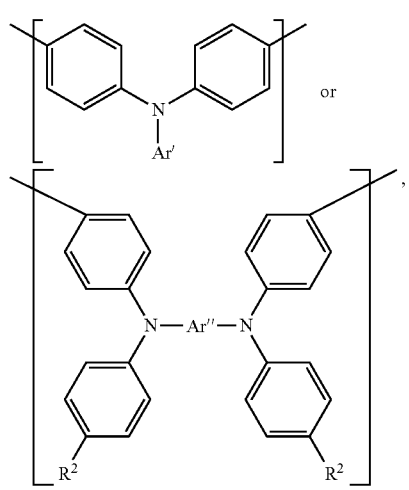

Ar' is

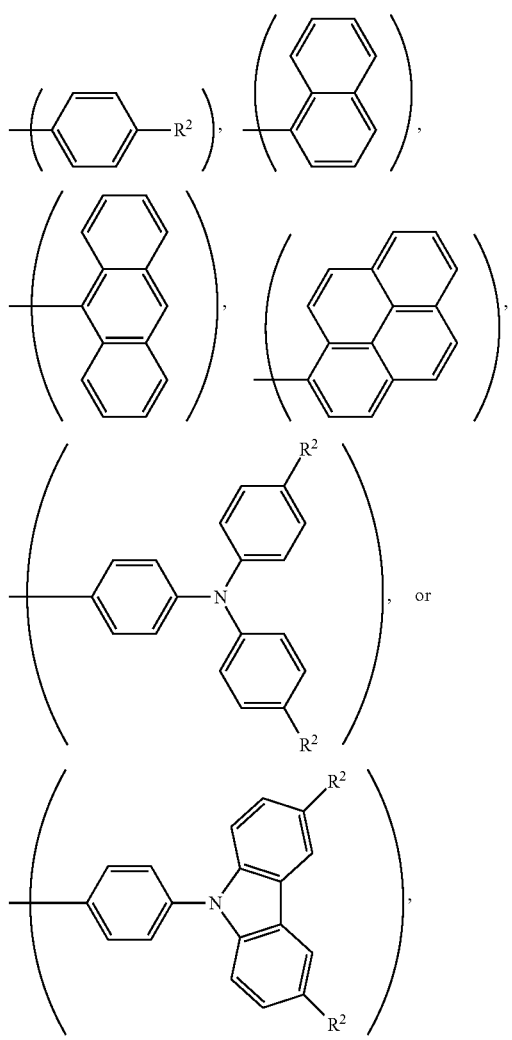

Ar'' is

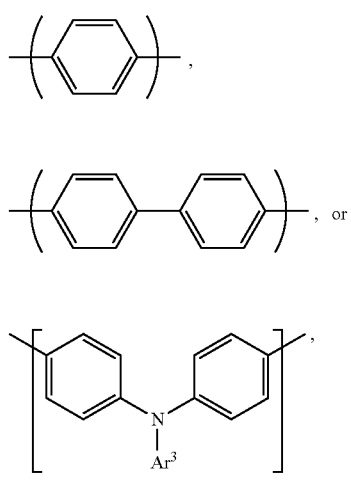

Ar³ is

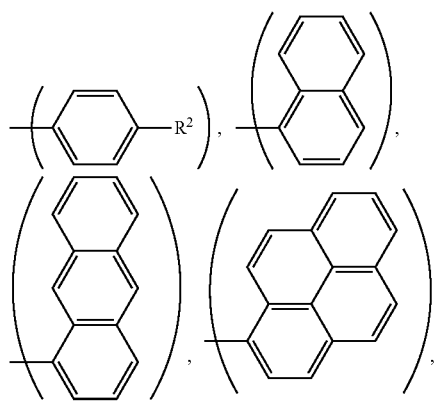

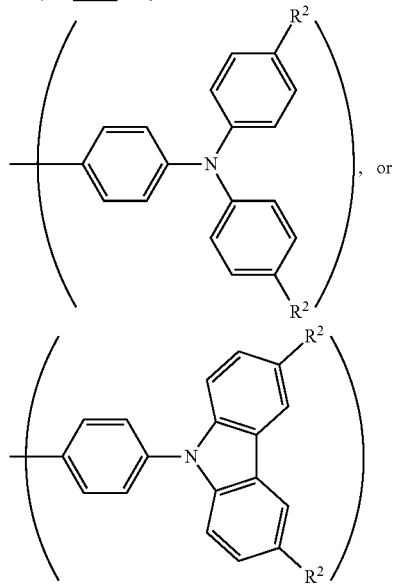

and R² can be H, an alkyl, or an alkoxy.

In one embodiment, R¹ can be a C1-8 alkyl group.

In one embodiment, R¹ can be a C1-4 alkyl group.

In one embodiment, R² can be hydrogen, a C1-8 alkyl group, or a C1-8 alkoxy group.

In one embodiment, R² can be a C1-4 alkyl group, or a C1-4 alkoxy group.

In one embodiment, R³ can be hydrogen, a C1-8 alkyl group, or a C1-8 alkoxy group.

In one embodiment, R³ can be a C1-4 alkyl group, or a C1-4 alkoxy group.

The organic compounds can be prepared from the reaction of carboxylic acids with diamine. The intermediate product of the diamine, dinitro can be prepared according to literature methods and then the diamine can be obtained from the dinitro through reduction as shown in Formula 2 or 3 below (J. Polym. Sci. Part A: Polym. Chem. 2006, 44, pp 4579-4592, the entire disclosure of which is incorporated herein by reference). Ar', Ar", and R2 in Formulas 2 and 3 have the same meaning as defined in the above Formula (1). The aforementioned organic compounds are applicable as an electrochromic element, a semiconductor, a solar cell, an organic electroluminescent element, an active substance of a non-linear material, etc.

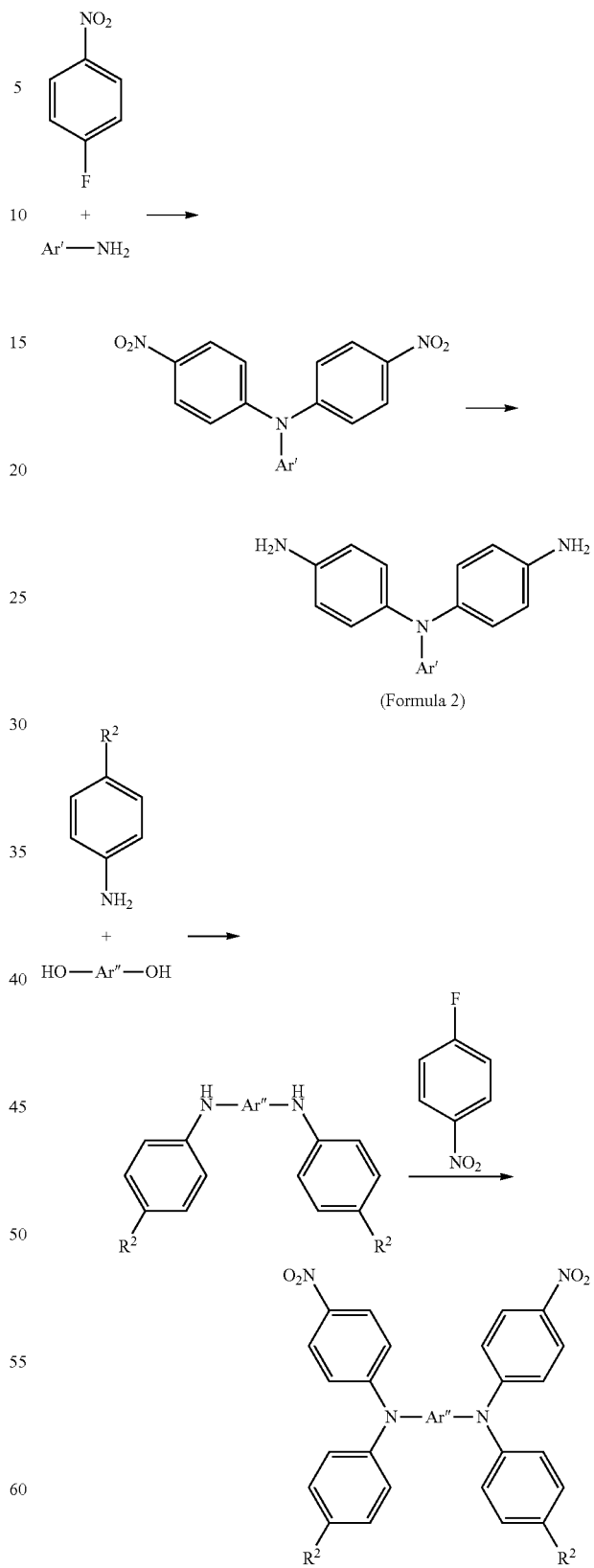

(Formula 2)

-continued

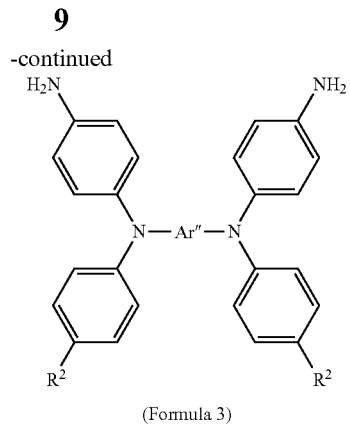

(Formula 3)

In accordance with some embodiments of the disclosure, the disclosure also provides an organic compound having a structure represented by the following formula:

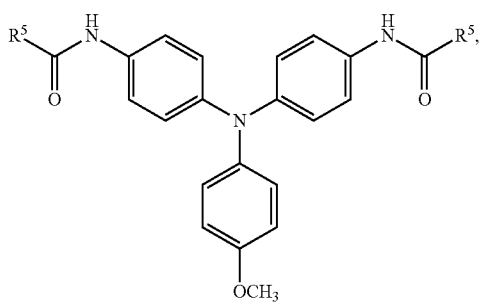

wherein $R^5$ can be a C1-8 alkyl group.

In accordance with some embodiments of the disclosure, the disclosure also provides an organic compound having a structure represented by the following formula:

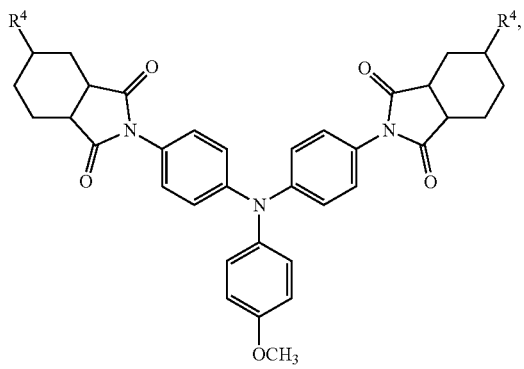

wherein $R^4$ can be a C1-8 alkyl group.

In accordance with some embodiments of the disclosure, the disclosure also provides an organic compound having a structure represented by the following formula:

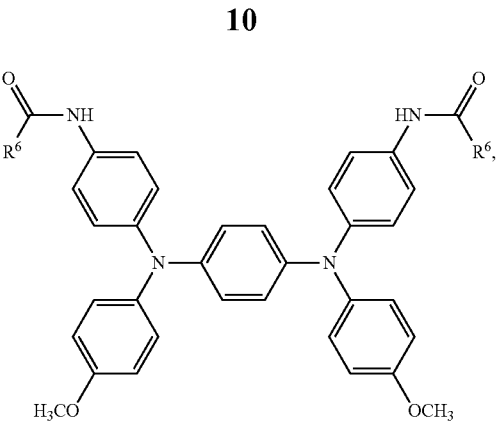

wherein $R^6$ can be a C1-8 alkyl group.

In accordance with some embodiments of the disclosure, the disclosure also provides an organic compound having a structure represented by the following formula:

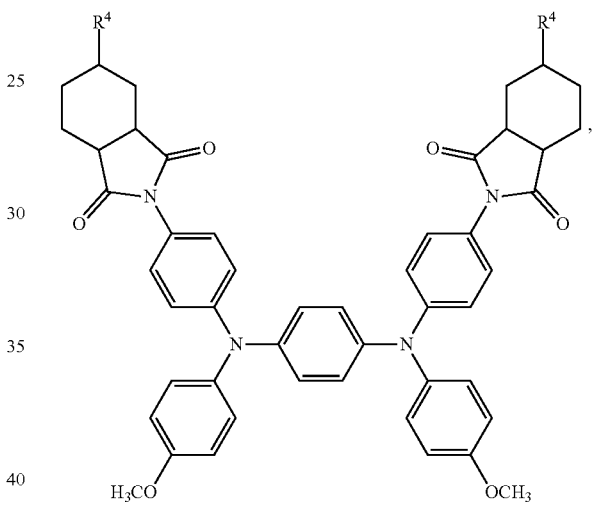

wherein $R^4$ can be a C1-8 alkyl group.

According to an embodiment of the disclosure, the aforementioned organic compound can be used as a first oxidizable compound which can be combined with a reducible compound, an electrolyte and a solvent to form a light modulating composition. In one embodiment, the oxidizable compound and the electrolyte have a molar ratio of 1:1 to 1:20, and the reducible compound and the electrolyte have a molar ratio of 1:1 to 1:20.

In some embodiments, the electrolyte may contain at least one inert conducting salt. Examples of suitable inert conducting salts include lithium salts, sodium salts and tetraalkylammonium salts, such as tetrabutylammonium. Suitable solvents include solvents which are redox-inert at the voltages selected and which cannot dissociate to form electrophiles or nucleophiles or themselves react as sufficiently strong electrophiles or nucleophiles and thus could react with the colored ionic free radicals. Examples of suitable solvents include propylene carbonate (PC), gamma-Butyrolactone (GBL, γ-butyrolactone), acetonitrile, propionitrile, glutaronitrile, methylglutaronitrile, 3,3'-oxydipropionitrile, hydroxypropionitrile, dimethylformamide, N-methylpyrrolidone, sulfolane, 3-methylsulfolane or mixtures thereof. The concentration of the electrolyte can be between 0.01M and 1.5M.

In some embodiments, the reducible compound can be selected from the group consisting of

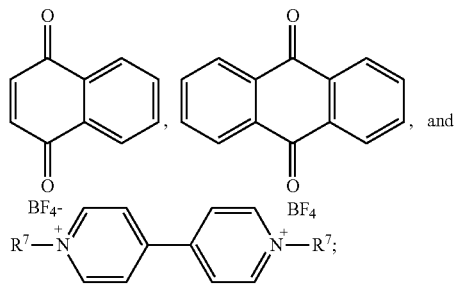

wherein R⁷ is a C1-C10 alkyl group.

In some embodiments of the disclosure, the oxidizable compound can include a second oxidizable compound, which can be

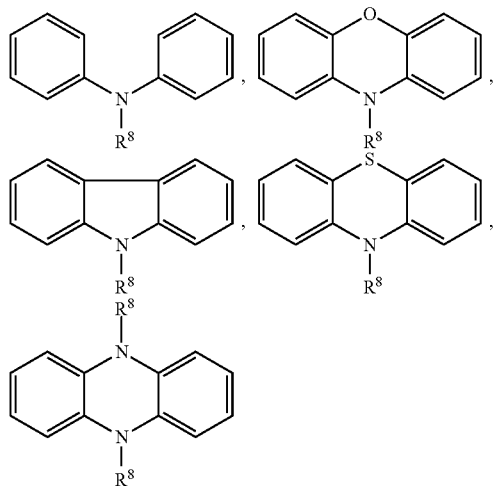

or the combinations thereof, wherein R⁸ is H or an alkyl group.

In accordance with some embodiments of the disclosure, a light modulating device can be provided. As shown in FIG. 1, the light modulating device includes a pair of electrodes, an isolating unit and a light modulating composition. The pair of electrodes 12, 18 includes a first transparent substrate 11 with a first transparent conductive layer 13 on a surface of the transparent substrate and a second transparent substrate 19 with a second transparent conductive layer 17 on a surface of the transparent substrate 19. The pair of electrodes 12, 18 is disposed by arranging the first transparent conductive layer 13 and second transparent conductive layer 17 to face each other. The isolating unit 14 is inserted and sealed up between the first and second transparent conductive layers 13, 17 to form a cell 15. Then, via a port (not shown) on the isolating unit 14, the aforementioned light modulating composition is introduced into the cell 15. The port was sealed so that the light modulating device 10 is formed.

In some embodiments of the disclosure, the transparent substrates can be made of glass or plastic such as polycarbonate. The conductive layer can be made of indium tin oxide (ITO), antimony- or fluorine-doped tin oxide, antimony- or aluminum-doped zinc oxide, tin oxide or conductive organic polymers such as, for example, optionally substituted polythienyls, polypyrroles, polyanilines, polyacetylene.

In some embodiments of the disclosure, the isolating unit can be formed by blending spacer elements with a thermosetting or photochemically curable adhesive. Spacer elements can be small spherules of plastic or glass or certain sand fractions In some embodiments of the disclosure, the distance from the first conducting material layer to the second conducting material layer can be between 10 μm to 200 μm.

The light modulating device will change from colorless to a specific color (e.g. yellow green, sky blue, blue, deep blue, or deep purple) after being applied with a suitable voltage. The specific color and the voltage depend on the chemical structure of the organic oxidizable compound of the light modulating composition. After the voltage is switched off, the cell contents completely bleach once more within 1 min. The experiments described below show that the cell still worked satisfactorily after operating 10,000 coloring/bleaching cycles. In other words, the light modulating composition solution has good stability.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

In the following Examples, the electrochemical analysis was performed by CH Instruments 612C to scan potentials of the thin film. The cyclic voltammetry (CV) was performed by a three-electrode system, wherein the ITO glass served as a working electrode (the coated polymer had an area of about 2.0 cm×0.8 cm), an Ag/AgCl electrode (in saturated KCl solution) served as a reference electrode, a platinum wire served as an auxiliary electrode, 0.1M of tetrabutylammonium perchloride solution (in acetonitrile) served as an electrolyte, and a scan rate was 50 mV/s. The average value of a redox potential was defined as a half-wave potential.

Example A1: Preparation of Organic Compound (A1)

10.0 g of 4-methoxytriphenylamine-based diamine (compound (I)) and 6.4 g of isobutyric acid (compound (II)) were mixed in a reaction flask. 25 ml of Dimethylacetamide (DMAc) serving as a solvent was added into the reaction flask, and 20.3 g of Triphenyl Phosphate (TPP) and 5.68 g of pyridine serving as a catalyst were then added into the reaction flask. The mixture in the reaction flask was heated to 105° C. for 4 hours, and then cooled down to room temperature. The cooled reaction mixture was poured into ethanol to precipitate a solid, and then filtered to collect the solid. The solid was washed by water and then dried, a compound (A1) (white solid) was obtained. The synthesis pathway of the above reaction was as follows:

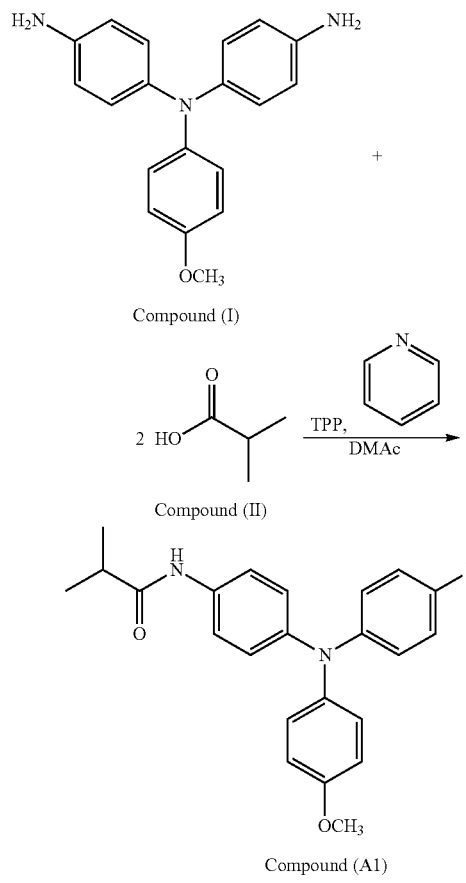

Compound (A1)

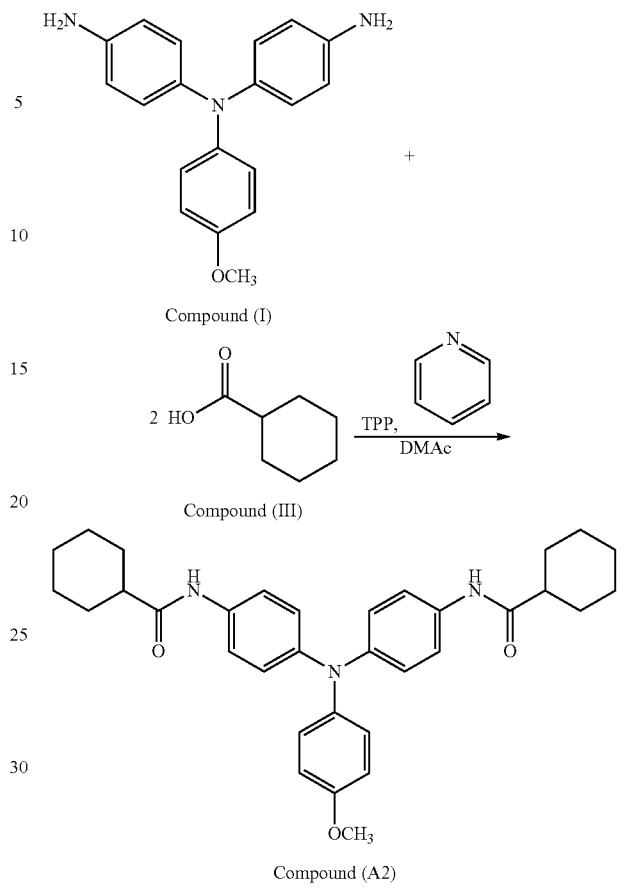

Compound (A2)

The physical measurement of the compound (A1) is listed below: 1H NMR (500 MHz, DMSO-d$^6$): δ 1.02 (d, J=7.0 Hz, 6H), 2.49 (m, 2H), 3.66 (s, 3H), 6.78 (d, J=9.0 Hz, 4H), 6.81 (d, J=8.5 Hz, 2H), 6.87 (d, J=8.5 Hz, 2H), 7.41 (d, J=9.0 Hz, 4H), 9.65 (s, 2H). 13C NMR (125 MHz, DMSO-d6): δ 19.5, 34.8, 55.2, 114.8, 120.4, 122.9, 125.7, 133.9, 140.5, 143.0, 155.2, 174.8. Anal. calcd for $C_{27}H_{31}N_3O_3$: C, 72.78; H, 7.01; N, 9.43; found: C, 72.69; H, 7.03; N, 9.51.

Figure 2:
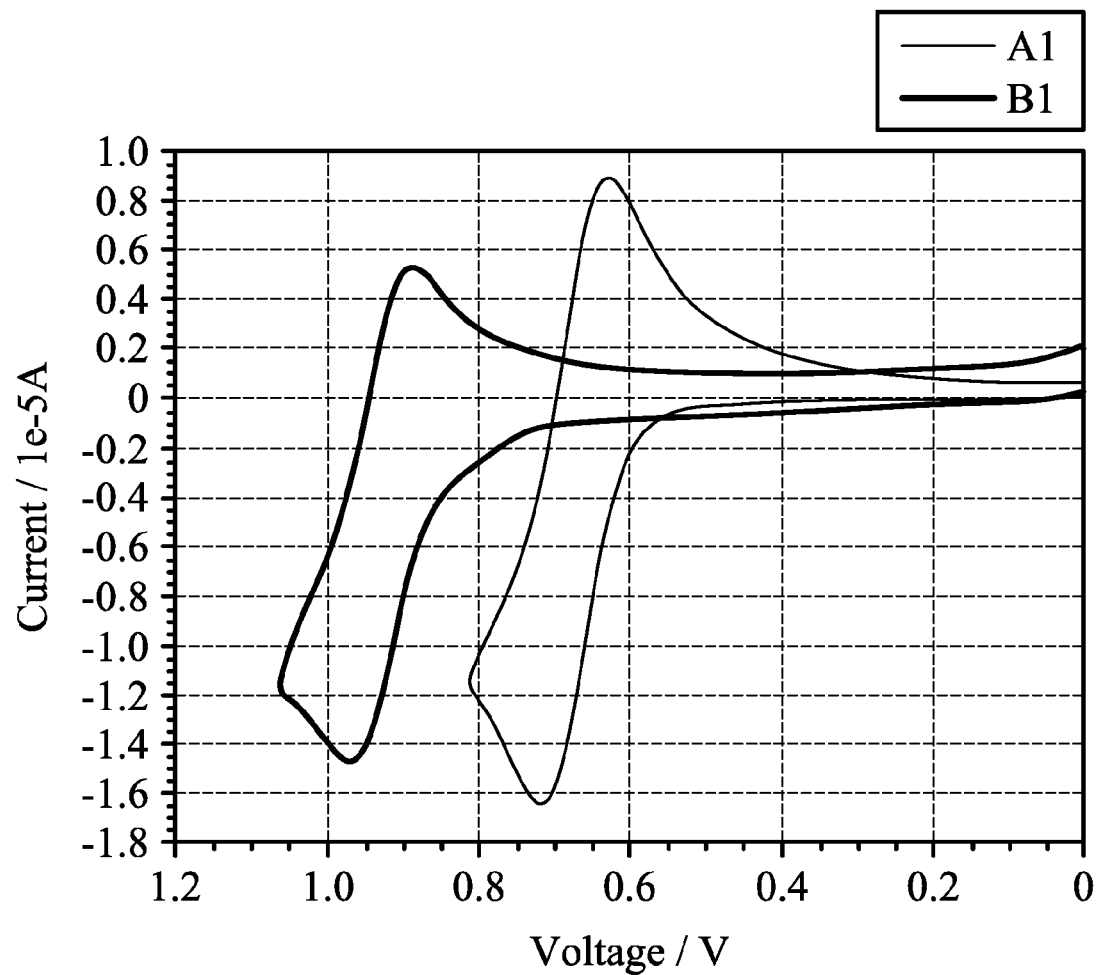
FIG. 2 shows cyclic voltammetry diagrams of organic compounds in the Examples of the disclosure.
Figure 4:
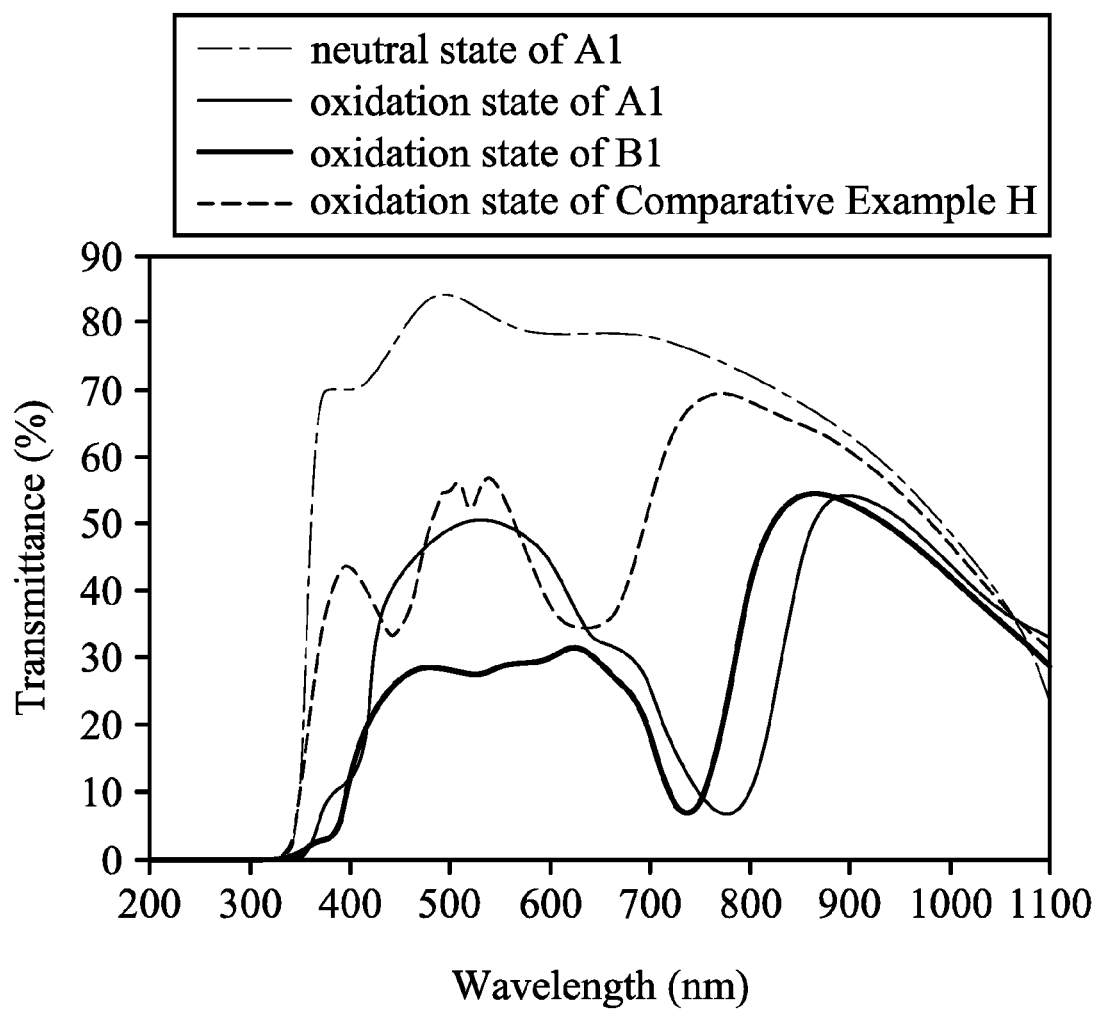
FIG. 4 shows transmittance spectra of neutral and oxidation state of organic compounds in the Examples of the disclosure.

The compound (A1) has a cyclic voltammetry CV diagram as shown in FIG. 2, redox potential as tabulated in Table 1 below, the transmittance spectrum of neutral and oxidation state as shown in FIG. 4, and the transmittance of neutral and oxidation state at different wavelengths as tabulated in Table 2 below.

Example A2: Preparation of Organic Compound (A2)

10.0 g of 4-methoxytriphenylamine-based diamine (compound (I)) and 8.4 g of cyclohexanoic acid (compound (III)) were mixed in a reaction flask. 25 ml of Dimethylacetamide (DMAc) serving as a solvent was added into the reaction flask, and 20.3 g of Triphenyl Phosphate (TPP) and 5.68 g of pyridine serving as a catalyst were then added into the reaction flask. The mixture in the reaction flask was heated to 105° C. for 4 hours, and then cooled down to room temperature. The cooled reaction mixture was poured into ethanol to precipitate a solid, and then filtered to collect the solid. The solid was washed by water and then dried, a compound (A2) (white solid) was obtained. The synthesis pathway of the above reaction was as follows:

The physical measurement of the compound (A2) is listed below: 1H NMR (500 MHz, DMSO-d$^6$) δ 1.13-1.44 (m, 10H), 1.63-1.79 (m, 10H), 2.29 (t, 2H), 3.72 (s, 3H), 6.84 (d, J=9.0 Hz, 4H), 6.88 (d, J=8.5 Hz, 2H), 6.95 (d, J=8.5 Hz, 2H), 7.48 (d, J=9.0 Hz, 4H), 9.67 (s, 2H). 13C NMR (125 MHz, DMSO-d$^6$): δ 13.9, 22.0, 25.1, 28.5, 28.6, 31.2, 55.2, 114.8, 120.2, 122.8, 125.8, 140.5, 143.0, 155.24, 170.8. Anal. calcd for $C_{33}H_{39}N_3O_3$: C, 75.4; H, 7.48; N, 7.99; found C, 74.8; H, 7.45; N, 7.87.

The compound (A2) has redox potential as tabulated in Table 1 below, transmittance of neutral and oxidation state at different wavelengths as tabulated in Table 2 below.

Example A3: Preparation of Organic Compound (A3)

10.0 g of 4-methoxytriphenylamine-based diamine (compound (I)) and 9.45 g of octanoic acid (compound (IV)) were mixed in a reaction flask. 25 ml of Dimethylacetamide (DMAc) serving as a solvent was added into the reaction flask, and 20.3 g of Triphenyl Phosphate (TPP) and 5.68 g of pyridine serving as a catalyst were then added into the reaction flask. The mixture in the reaction flask was heated to 105° C. for 4 hours, and then cooled down to room temperature. The cooled reaction mixture was poured into ethanol to precipitate a solid, and then filtered to collect the solid. The solid was washed by water and then dried, a compound (A3) (white solid) was obtained. The synthesis pathway of the above reaction was as follows:

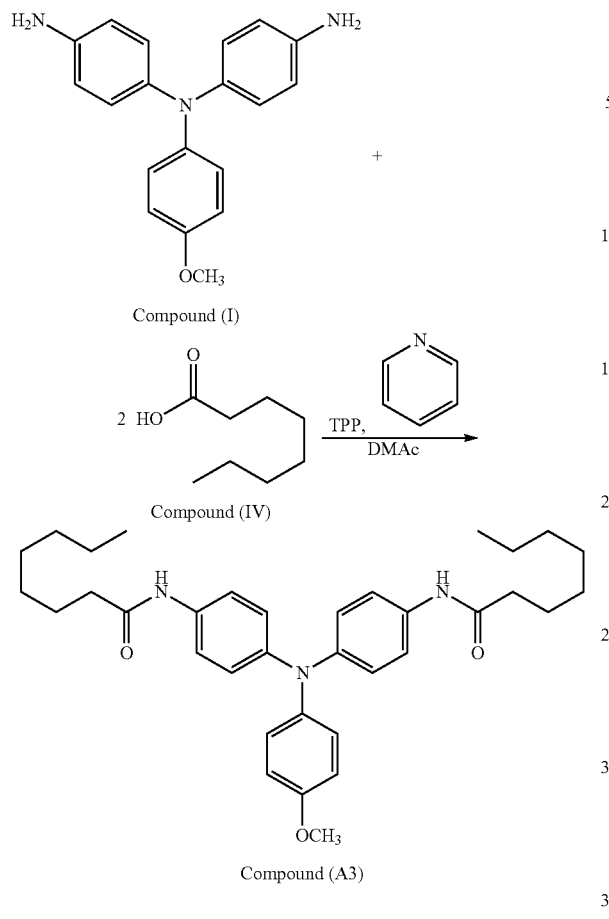

Compound (A3)

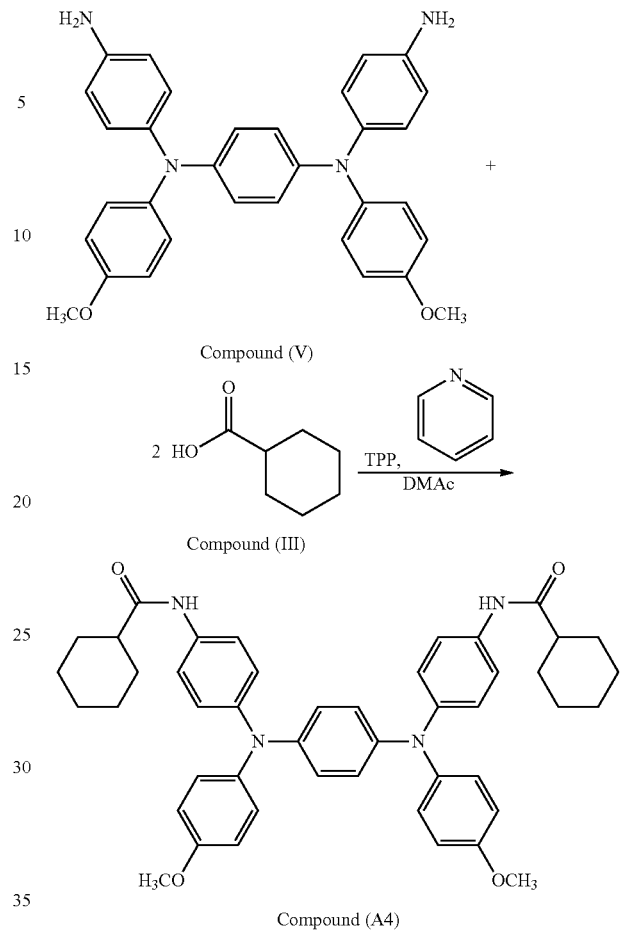

Compound (A4)

The physical measurement of the compound (A3) is listed below: 1H NMR (500 MHz, DMSO-d$^6$): δ 0.86 (t, 6H), 1.26-1.59 (m, 16H), 2.51 (t, 4H), 3.73 (s, 3H), 6.85 (d, J=9.0 Hz, 4H), 6.88 (d, J=8.5 Hz, 2H), 6.95 (d, J=8.5 Hz, 2H), 7.47 (d, J=9.0 Hz, 4H), 9.76 (s, 2H). 13C NMR (125 MHz, DMSO-d$^6$): δ 13.9, 22.0, 25.2, 28.5, 28.6, 31.2, 55.2, 114.8, 120.2, 122.8, 125.8, 133.8, 140.5, 143.0, 155.2, 170.8. Anal. calcd for $C_{33}H_{43}N_3O_3$: C, 74.82; H, 8.18; N, 7.93; found: C, 74.89; H, 8.09; N, 7.88.

The compound (A3) has redox potential as tabulated in Table 1 below, the transmittance of neutral and oxidation state at different wavelengths as tabulated in Table 2 below.

Example A4: Preparation of Organic Compound (A4)

[please add a paragraph number here] 10.0 g of 4-methoxypentaphenylamine-based diamine (compound (V)) and 5.1 g of cyclohexanoic acid (compound (III)) were mixed in a reaction flask. 25 ml of Dimethylacetamide (DMAc) serving as a solvent was added into the reaction flask, and 20.3 g of Triphenyl Phosphate (TPP) and 5.68 g of pyridine serving as a catalyst were then added into the reaction flask. The mixture in the reaction flask was heated to 105° C. for 4 hours, and then cooled down to room temperature. The cooled reaction mixture was poured into ethanol to precipitate a solid, and then filtered to collect the solid. The solid was washed by water and then dried, a compound (A4) (white solid) was obtained. The synthesis pathway of the above reaction was as follows:

The physical measurement of the compound (A4) is listed below: 1H NMR (500 MHz, DMSO-d$^6$) δ 1.24-1.38 (m, 10H), 1.40-1.75 (m, 10H), 1.77 (t, 2H), 3.72 (s, 6H), 6.79 (s, 4H), 6.87-6.88 (m, 6H), 6.97 (d, J=8.5 Hz, 2H), 7.47 (d, J=9.0 Hz, 4H), 9.69 (s, 2H). 13C NMR (125 MHz, DMSO-d$^6$) δ 25.2, 25.4, 29.1, 44.7, 55.2, 114.8, 120.3, 123.0, 123.2, 125.9, 134.0, 140.4, 142.0, 142.9, 155.3, 173.8. Anal. calcd for $C_{46}H_{52}N_4O_4$: C, 76.21; H, 7.23; N, 7.73; found C, 75.95; H, 7.29; N, 7.75.

Figure 3:
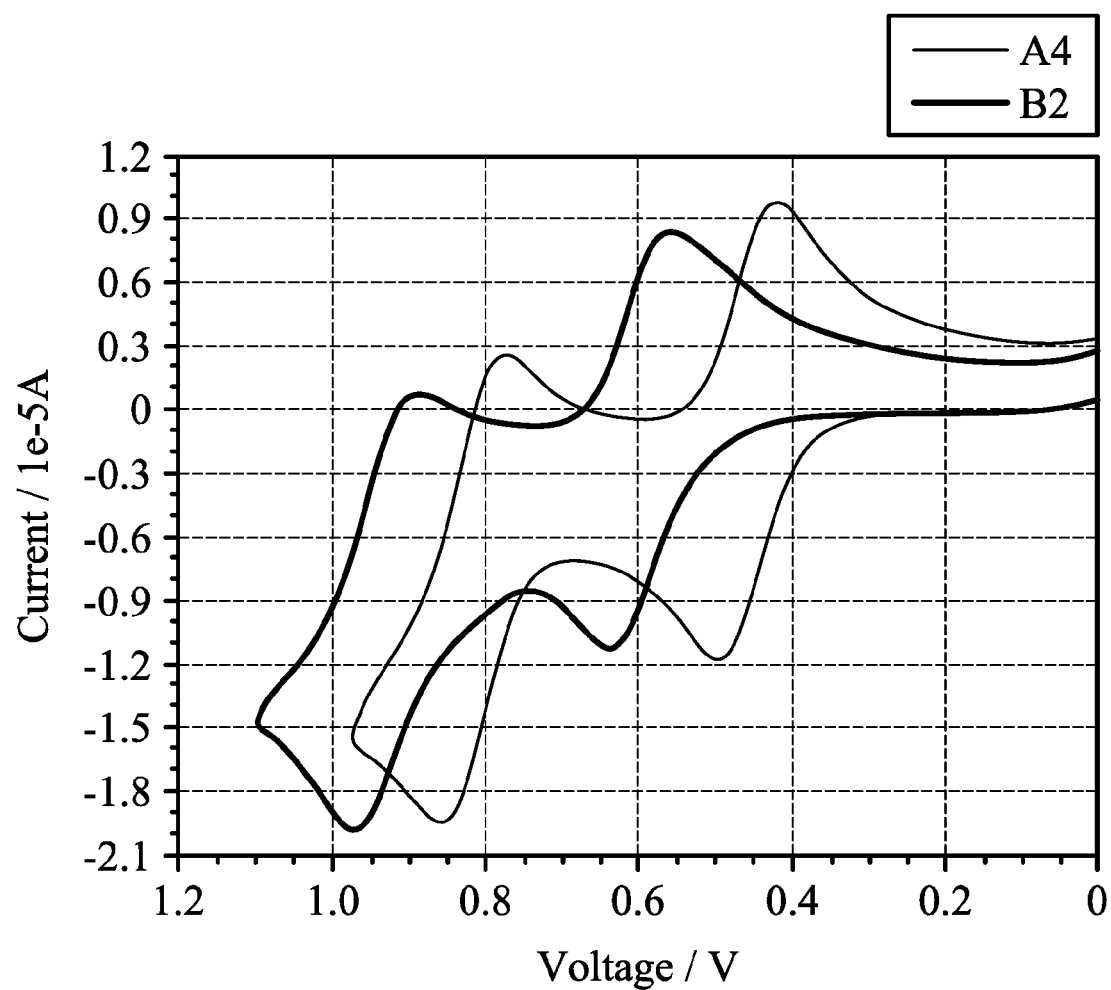
FIG. 3 shows cyclic voltammetry diagrams of organic compounds in the Examples of the disclosure.
Figure 5:
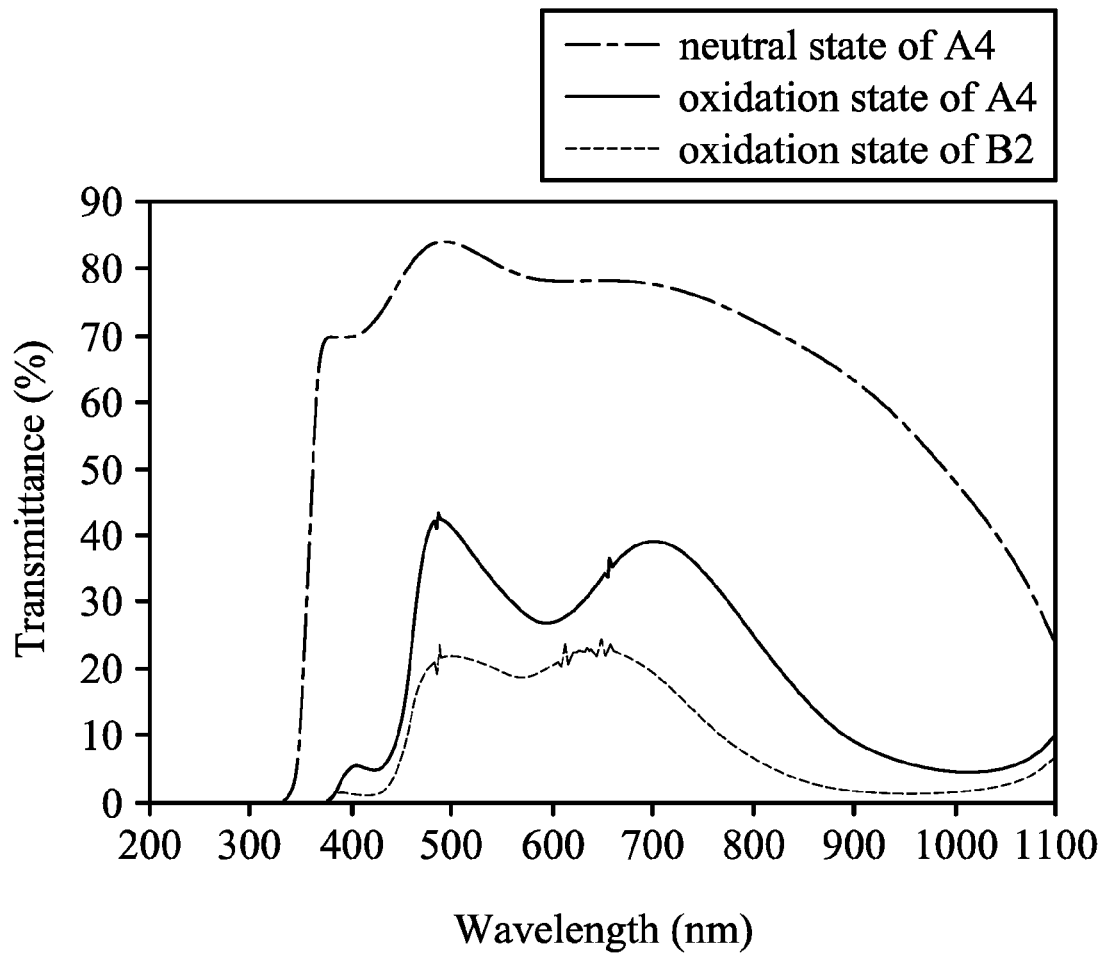
FIG. 5 shows transmittance spectra of neutral and oxidation state of organic compounds in the Examples of the disclosure.

The compound (A4) has a cyclic voltammetry CV diagram as shown in FIG. 3, redox potential as tabulated in Table 1 below, the transmittance spectrum of neutral and oxidation state as shown in FIG. 5, and the transmittance of neutral and oxidation state at different wavelengths as tabulated in Table 2 below.

Example B1: Preparation of Organic Compound (B1)

1.50 g of 4-methoxytriphenylamine-based diamine (compound (I)) and 1.70 g of hexahydrophthalic anhydride (compound (VI)) were mixed in a reaction flask. 2.5 ml of Dimethylacetamide (DMAc) serving as a solvent was added into the reaction flask, and a little of Isoquinoline serving as a catalyst was then added into the reaction flask. The mixture in the reaction flask was heated to 210° C. for 5 hours, and then cooled down to room temperature. The cooled reaction mixture was diluted by methanol and poured into water to precipitate a solid, and then filtered to collect the solid. The solid was washed by water and then dried, a compound (B1) (beige solid) was obtained. The synthesis pathway of the above reaction was as follows:

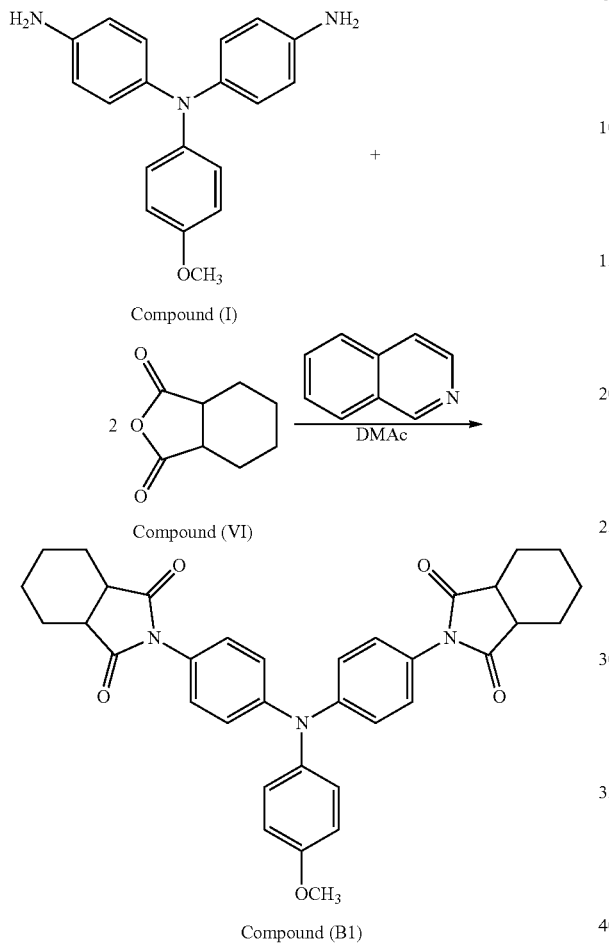

Compound (I)

Compound (VI)

Compound (B1)

The physical measurement of the compound (B1) is listed below: 1H NMR (500 MHz, DMSO-d$^6$) δ 1.38 (m, 4H), 1.73 (q, 4H), 3.08 (q, 2H), 3.75 (s, 3H), 6.97 (d, J=9.5 Hz, 2H), 7.02 (d, J=9.0 Hz, 4H), 7.11 (d, J=9.5 Hz, 2H), 7.14 (d, J=9.0 Hz, 4H). 13C NMR (125 MHz, DMSO-d6): δ 21.4, 23.4, 55.3, 115.4, 122.0, 126.2, 127.9, 128.1, 139.1, 147.0, 156.7, 178.8. Anal. calcd for $C_{35}H_{35}N_3O_5$: C, 72.77; H, 6.11; N, 7.27; found C, 72.35; H, 6.16; N, 7.25.

The compound (B1) has a cyclic voltammetry CV diagram as shown in FIG. 2, redox potential as tabulated in Table 1 below, the transmittance spectrum of neutral and oxidation state as shown in FIG. 4, and the transmittance of neutral and oxidation state at different wavelengths as tabulated in Table 2 below.

Example B2: Preparation of Organic Compound (B2)

5.0 g of 4-methoxypentaphenylamine-based diamine (compound (V)) and 3.06 g of hexahydrophthalic anhydride (compound (VI)) were mixed in a reaction flask. 7.5 ml of dimethylacetamide (DMAc) serving as a solvent was added into the reaction flask, and a little of isoquinoline serving as a catalyst was then added into the reaction flask. The mixture in the reaction flask was heated to 210° C. for 5 hours, and then cooled to room temperature. The cooled reaction mixture was diluted by methanol and poured into water to precipitate a solid, and then filtered to collect the solid. The solid was washed by water and then dried, a compound (B2) (beige solid) was obtained. The synthesis pathway of the above reaction was as follows:

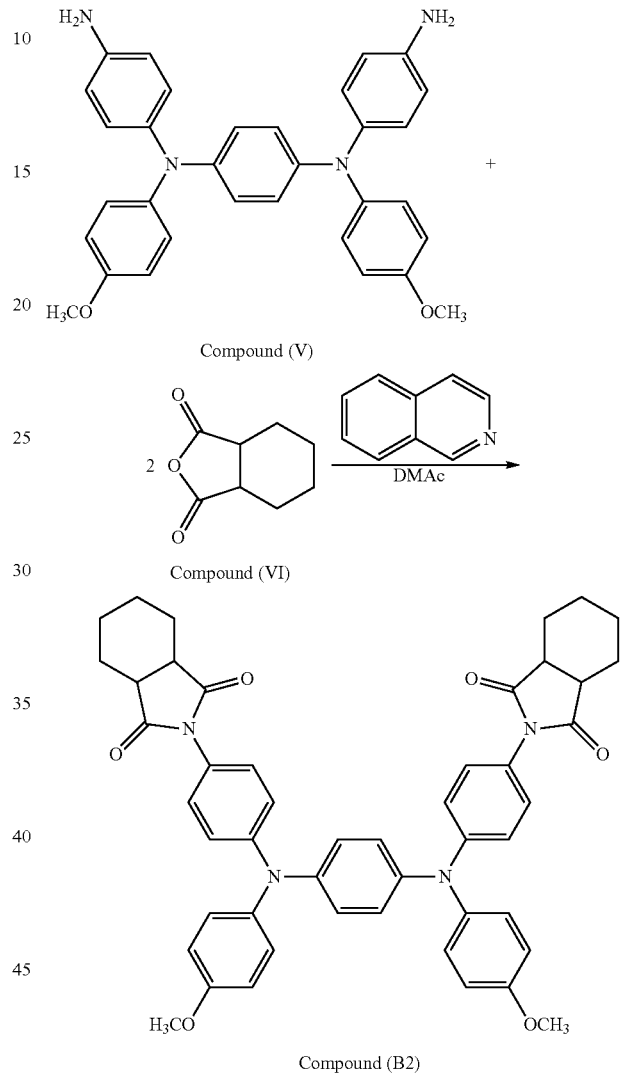

Compound (V)

Compound (VI)

Compound (B2)

The physical measurement of the compound (B2) is listed below: 1H NMR (500 MHz, DMSO-d$^6$) δ 1.36~1.42 (m, 8H), 1.70~2.00 (m, 8H), 3.08 (t, 4H), 3.74 (s, 6H), 6.92~7.10 (m, 20H). 13C NMR (125 MHz, DMSO-d$^6$): δ 21.3, 21.4, 23.3, 55.2, 115.2, 120.2, 124.9, 125.0, 127.5, 127.7, 139.4, 142.2, 147.6, 156.3, 178.8. Anal. calcd for $C_{48}H_{46}N_4O_6$: C, 74.40; H, 5.98; N, 7.23; found C, 74.21; H, 6.03; N, 7.27.

The compound (B2) has a cyclic voltammetry CV diagram as shown in FIG. 3, redox potential as tabulated in Table 1 below, the transmittance spectrum of neutral and oxidation state as shown in FIG. 5, and the transmittance of neutral and oxidation state at different wavelengths as tabulated in Table 2 below.

TABLE 1

| Example | $E1_{1/2}$ (V)[a] | $E2_{1/2}$ (V)[b] |
|---|---|---|
| A1 | 0.68 (teal) | — |
| A2 | 0.67 (teal) | — |
| A3 | 0.68 (teal) | — |
| A4 | 0.46 (green) | 0.81 (blue) |
| B1 | 0.93 | — |
| B2 | 0.60 (green) | 0.94 (blue) |

[a]$E1_{1/2}$ (V) is a half-wave potential at the first oxidation state.
[b]$E2_{1/2}$ (V) is a half-wave potential at the second oxidation state.

Table 1, Table 2 and FIG. 1 show that triphenylamine system (compounds A1-A3 and B1) only had an oxidation-reducing peak and pentaphenyldiamine system (compounds A1-A3 and B1) had two oxidation-reducing peaks. The difference of electrical potential peak between the amido group and the imido group was large (A1 vs. B1, and A4 vs. B2). By using different terminal functional groups, the redox potential of an organic compound can be modulated.

TABLE 2

| | Transmittance (%) | | | | | |
|---|---|---|---|---|---|---|
| Example/T(%) | 450 nm | 600 nm | 700 nm | 800 nm | 900 nm | 1000 nm |
| neutral state of A1 | 78.5 | 78.5 | 78.1 | 72.7 | 63.8 | 49.7 |
| oxidation state of A1 | 74.5 | 67.5 | 50.2 | 36.1 | 62.5 | 49.7 |
| neutral state of A2 | 79.8 | 78.7 | 78.1 | 72.6 | 63.6 | 49.2 |
| oxidation state of A2 | 60.9 | 55.1 | 33.9 | 17.6 | 57.3 | 45.1 |
| neutral state of A3 | 78.4 | 77.8 | 77.1 | 71.4 | 62.3 | 47.6 |
| oxidation state of A3 | 66.2 | 61.0 | 40.9 | 19.3 | 60.5 | 49.0 |
| neutral state of B1 | 78.6 | 78.2 | 77.6 | 71.9 | 62.8 | 47.7 |
| oxidation state of B1 | 53.9 | 54.1 | 38.6 | 57.4 | 59.9 | 46.7 |
| neutral state of A4 | 74.3 | 75.8 | 74.9 | 69.2 | 60.1 | 45.5 |
| oxidation state of A4 | 13.1 | 26.8 | 38.8 | 24.5 | 9.08 | 4.65 |
| neutral state of B2 | 76.7 | 77.0 | 76.6 | 71.2 | 61.3 | 46.4 |
| oxidation state of B2 | 6.98 | 20.3 | 19.2 | 6.73 | 1.81 | 1.51 |
| neutral state of PSN[c] | 79.0 | 78.0 | 77.3 | 71.3 | 61.9 | 47.1 |
| oxidation state of PSN | 34.7 | 37.1 | 54.2 | 67.7 | 60.4 | 46.5 |

[c]PSN is phenothiazine as a comparative compound

Table 2, 3 and FIG. 4 show that the shielding effect of the triphenylamine system (compounds A1 and B1) was better than the shielding effect of PSN in the visible region. The pentaphenyldiamine system had absorption in the visible region and good heat-ray absorption in the NIR region. In other words, the pentaphenyldiamine system compounds had property of anti-ultraviolet activity and absorption in the NIR region.

Example C1: Preparation of a Light Modulating Device

Tetrabutyl ammonium tetrafluoroborate (TBABF$_4$) was dissolved in propylene carbonate (PC) to form a 0.5 M solution. Next, compound A2 and viologen [(HV(BF$_4$)$_2$] was dissolved in the above solution to form a light modulating composition solution, wherein the concentration of compound A2 was 0.1M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm. The light modulating device was applied a voltage of 1.4V to measure the transmittance of the device as tabulated in Table 3 below.

Example C2: Preparation of a Light Modulating Device

Figure 6:
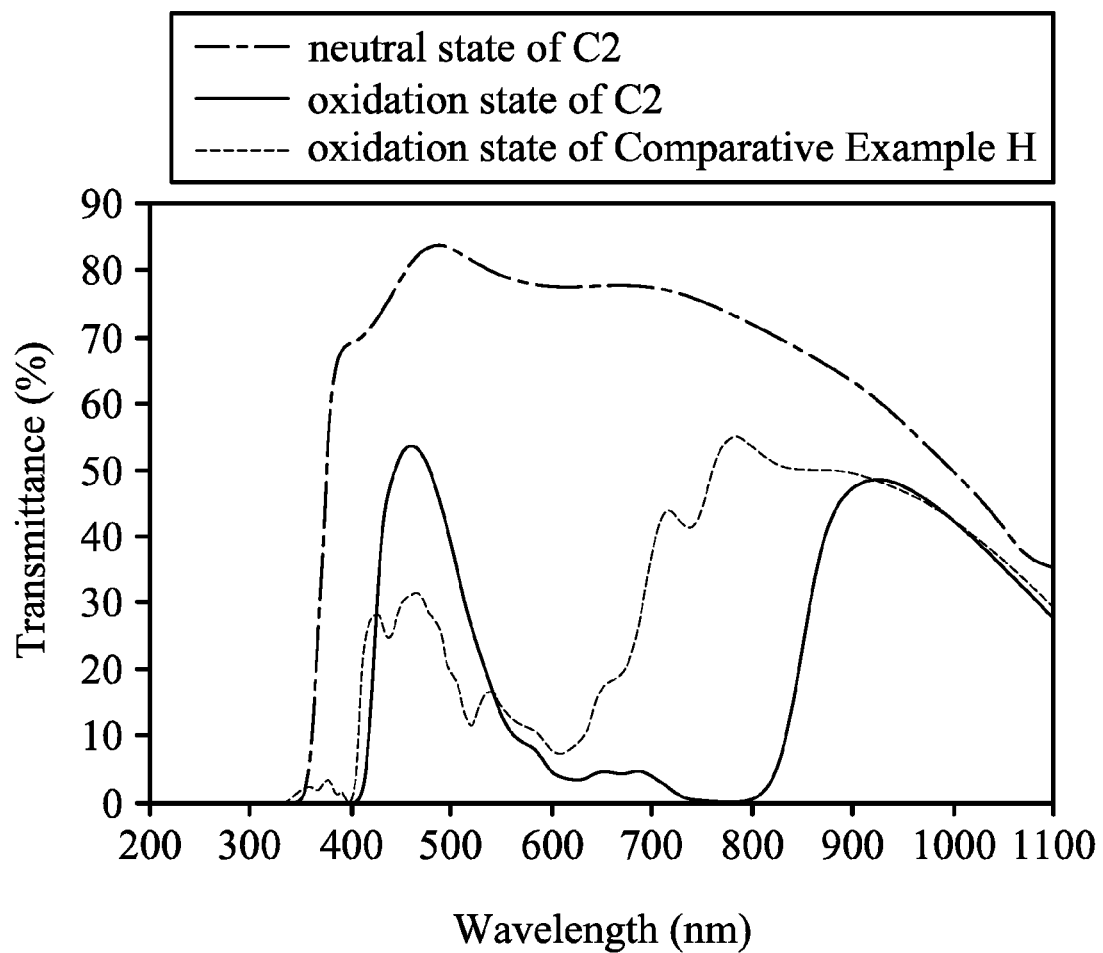
FIG. 6 shows transmittance spectra of neutral and oxidation state of light modulating device in the Examples of the disclosure.

Tetrabutyl ammonium tetrafluoroborate (TBABF$_4$) was dissolved in propylene carbonate (PC) to form a 0.5 M solution. Next, compound B1 and viologen [(HV(BF$_4$)$_2$] were dissolved in the above solution to form a light modulating composition solution, wherein the concentration of compound B1 was 0.1M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm. The light modulating device was applied a voltage of 1.6V to measure the transmittance of the device as tabulated in Table 3 below. The transmission spectrum of the neutral state (off-state) and oxidation state (on-state) of the device obtained as shown in FIG. 6.

Example C3: Preparation of a Light Modulating Device

Tetrabutyl ammonium tetrafluoroborate (TBABF4) was dissolved in propylene carbonate (PC) to form a 0.5 M solution. Next, compound A4 and viologen [(HV(BF4)2] was dissolved in the above solution to form a light modulating composition solution, wherein the concentration of compound A4 was 0.1M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm. The light modulating device was applied a voltage of 1.1V to measure the transmittance of the device as tabulated in Table 3 below.

Example C4: Preparation of a Light Modulating Device

Tetrabutyl ammonium tetrafluoroborate (TBABF4) was dissolved in propylene carbonate (PC) to form a 0.5 M solution. Next, compound B2 and viologen [(HV(BF4)2] was dissolved in the above solution to form a light modulating composition solution, wherein the concentration of compound B2 was 0.1M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 m. The light modulating device was applied a voltage of 1.3V to measure the transmittance of the device as tabulated in Table 3 below.

TABLE 3

| Device | Operating voltage (V) | Transmittance (%) | | | | | |
|---|---|---|---|---|---|---|---|
| | | 450 nm | 600 nm | 700 nm | 800 nm | 900 nm | 1000 nm |
| neutral state of C1 | 0.00 | 76.1 | 76.4 | 76.4 | 71.7 | 63.6 | 50.8 |
| oxidation state of C1 | 1.30 | 46.6 | 2.65 | 1.66 | 0.15 | 41.9 | 38.8 |
| neutral state of C2 | 0.00 | 78.1 | 78.0 | 77.2 | 71.5 | 62.4 | 47.8 |
| oxidation state of C2 | 1.60 | 51.8 | 4.60 | 3.79 | 0.57 | 4.76 | 42.5 |
| neutral state of C3 | 0.00 | 77.2 | 76.4 | 76.1 | 70.7 | 61.9 | 48.0 |
| oxidation state of C3 | 1.10 | 8.00 | 2.46 | 23.4 | 18.9 | 4.70 | 1.84 |
| neutral state of C4 | 0.00 | 74.4 | 76.0 | 75.5 | 69.9 | 60.7 | 46.3 |
| oxidation state of C4 | 1.30 | 16.4 | 7.56 | 26.9 | 13.6 | 4.21 | 2.99 |
| neutral state of PSN | 0.00 | 78.1 | 76.4 | 76.5 | 71.2 | 62.2 | 47.6 |
| oxidation state of PSN | 1.30 | 29.2 | 7.72 | 38.0 | 53.2 | 49.1 | 41.9 |

Table 3 and FIG. 6 show that the shielding effect of the Examples with added viologen was increased at wavelength around 600 nm. The shielding effect of the pentaphenyldiamine system Example C3 and C4 were larger than the shielding effect of the compounds C1 and C2 at wavelength near 400-500 nm. Compared with PSN, all Examples had the shielding effect within the range of 350-800 nm because triphenylamine and pentaphenyldiamine systems had better conjugation properties.

Example D: Preparation of a Light Modulating Device

Tetrabutyl ammonium tetrafluoroborate (TBABF$_4$) was dissolved in propylene carbonate (PC) to form a 0.5 M solution. Next, compound A1 and viologen [(HV(BF$_4$)$_2$] was dissolved in the above solution to form a light modulating composition solution, wherein the concentration of compound A1 was 0.1M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm.

Figure 7:
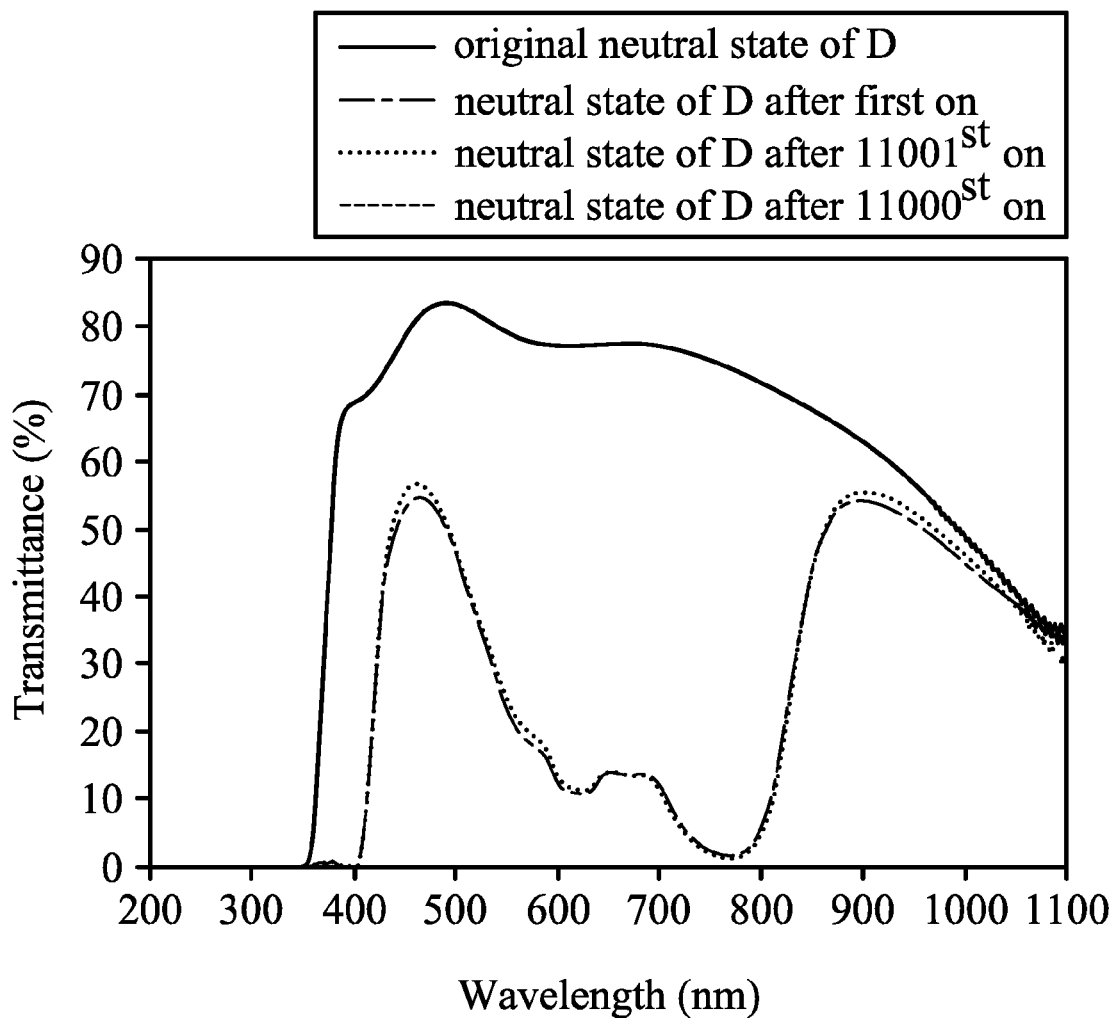
FIG. 7 shows transmittance spectra of a light modulating device after switching cycles in the Examples of the disclosure.

The light modulating device was applied a voltage of 1.3V for 3.250 seconds (on-state), and was applied a voltage of −1.3V for 0.375 seconds (off-state), and then stay at 0V for 3.675 seconds. Repeating the above method, the device was subjected to a cycle life test. As shown in the transmission spectrum of FIG. 7, the device turned from the original neutral state which was completely free of absorption to deep blue (oxidation state) in the visible region. Moreover, After 10,000 on/off cycles the device still worked and had transmission spectrum of on/off so that the device is stable. The transmission of the device at different wavelengths and at different state was obtained and as tabulated in Table 4 below.

TABLE 4

| Switching state | Transmittance(%) | | | | | |
|---|---|---|---|---|---|---|
| | 400 nm | 500 nm | 625 nm | 770 nm | 800 nm | 900 nm |
| Original neutral state 1st | 68.8 | 83.0 | 77.6 | 73.7 | 71.6 | 62.8 |
| After first on | 0.24 | 46.2 | 11.2 | 2.21 | 6.28 | 54.2 |
| After 11001st on | 0.31 | 46.9 | 11.7 | 1.80 | 5.43 | 55.5 |
| After 11000st off | 66.0 | 81.1 | 76.9 | 73.7 | 71.7 | 63.0 |

Example E: Preparation of a Transparent-Green Complementary Light Modulating Device Tetrabutyl ammonium tetrafluoroborate (TBABF$_4$) was dissolved in propylene carbonate (PC) to form a 0.5 M solution. Next, compound A1, 5,10-dimethylphenazine (DMP) and viologen [(HV(BF$_4$)$_2$] were dissolved in the above solution to form a light modulating composition solution, wherein the concentration of compound A1 was 0.025M, the concentration of DMP was 0.025M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm.

When the light modulating device was applied a voltage ad the spectrum shows that transmission of the device reduced to 10.4% at a wavelength of 450 nm. The device turned from transparent at neutral state to deep green (oxidation state). Moreover, after switching off the voltage the device can be recovered to transparent (off-state) in 1 second.

Example F: Preparation of a Transparent-Deep Blue Complementary Light Modulating Device Tetrabutyl ammonium tetrafluoroborate (TBABF$_4$) was dissolved in propylene carbonate (PC) to form a 0.5 M solution. Next, compound A1, phenothiazine (PSN), methylphenothiazine (MePSN) and viologen [(HV(BF$_4$)$_2$] were dissolved in the above solution to form a light modulating composition solution, wherein the concentration of compound A1 was 0.05M, the concentration of PSN was 0.05M, the concentration of MePSN was 0.05M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm.

When the light modulating device was applied a voltage gradually to 1.3V, the spectrum shows that transmission of the device reduced to 10.4% at a wavelength of 450 nm. The device turned from transparent at neutral state to deep green (oxidation state). Moreover, After switching off the voltage the device can be recovered to transparent (off-state) in 1 second.

Example G: Preparation of a Transparent-Dark Complementary Light Modulating Device Tetrabutyl ammonium tetrafluoroborate (TBABF$_4$) was dissolved in propylene carbonate (PC) to form a 0.5 M solution. Next, compound A1, phenothiazine (PSN), methylphenothiazine (MePSN) and viologen [(HV(BF$_4$)$_2$] were dissolved in the above solution to form a light modulating composition solution, wherein the concentration of compound A1 was 0.1M, the concentration of PSN was 0.1M, the concentration of MePSN was 0.1M and the concentration of viologen was 0.1M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm.

Figure 8:
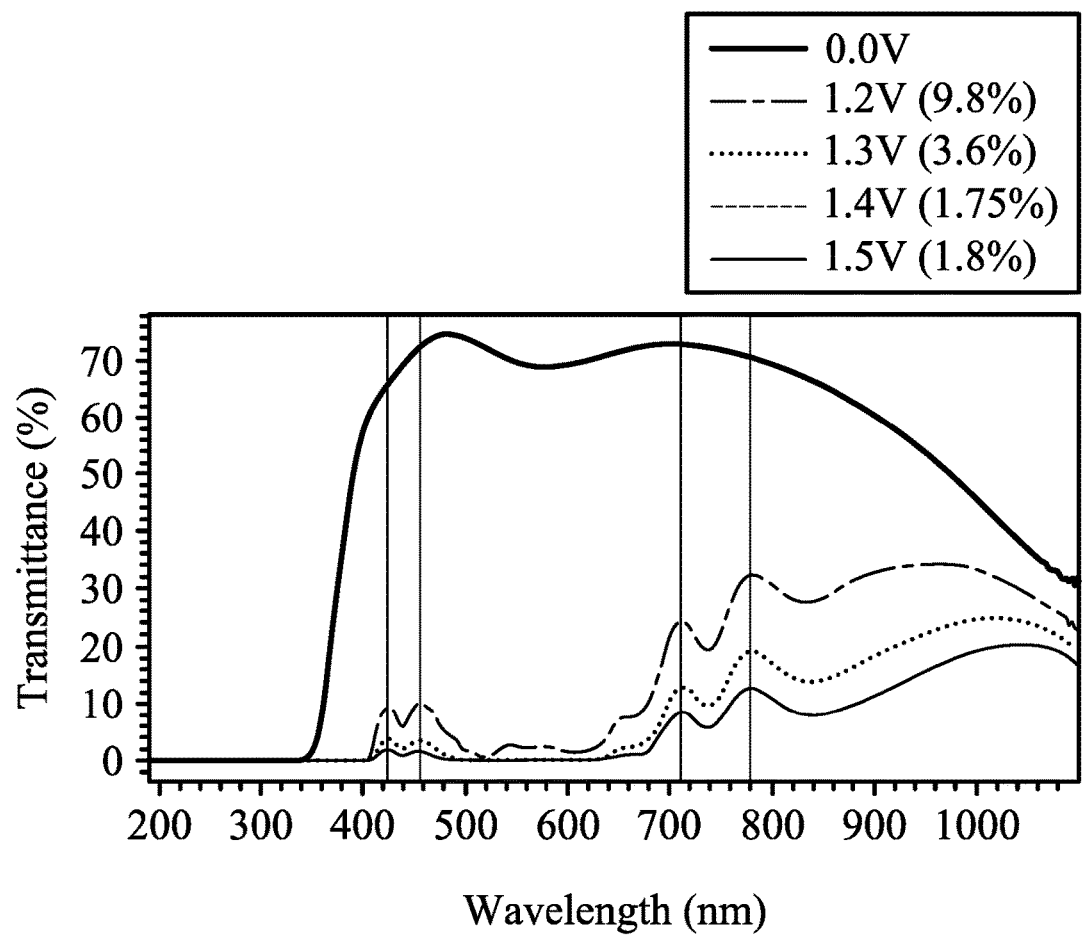
FIG. 8 shows transmittance spectra after different voltages applied to a light modulating device in the Examples of the disclosure.

When the light modulating device was applied a voltage gradually to 1.3V, the spectrum shows that transmission of the device reduced to 10.4% at a wavelength of 450 nm. The device turned from transparent at neutral state to deep green (oxidation state). The transmission spectrum of the device at different wavelengths and at different state was obtained and as shown in FIG. 8. Moreover, After switching off the voltage the device can be recovered to transparent (off-state) in 1 second.

Comparative Example H: Preparation of a Light Modulating Device

Tetrabutyl ammonium tetrafluoroborate (TBABF$_4$) was dissolved in propylene carbonate (PC) to form a 0.5 M solution. Next, phenothiazine (PSN) and viologen [(HV (BF$_4$)$_2$] was dissolved in the above solution to form a light modulating composition solution, wherein the concentration of PSN was 0.1M and the concentration of viologen was 0.05M. Two ITO conductive glass plates were cut to the desired size and the ITO layers of the plates face each other. An isolating unit was connected with the two ITO conductive glass plates to construct a cell. Via a port on the isolating unit, the aforementioned light modulating composition is introduced into the cell so that the cell was filled with the light modulating composition solution. The port was sealed so that the light modulating device is formed. The distance between the glass plates was about 50 μm. The transmittance spectrum of neutral and oxidation state was shown in FIG. 4, and the transmittance of neutral and oxidation state at different wavelength was tabulated in Table 2.

When the light modulating device was applied a voltage gradually to 1.3V, the device turned from transparent at neutral state to deep blue (oxidation state). The transmission spectrum of the device at different wavelengths and at different state was obtained and as shown in FIG. 6. The transmittance of the device at different wavelength was tabulated in Table 3.

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. An organic compound, having a structure as defined by Formula (I):

wherein X is

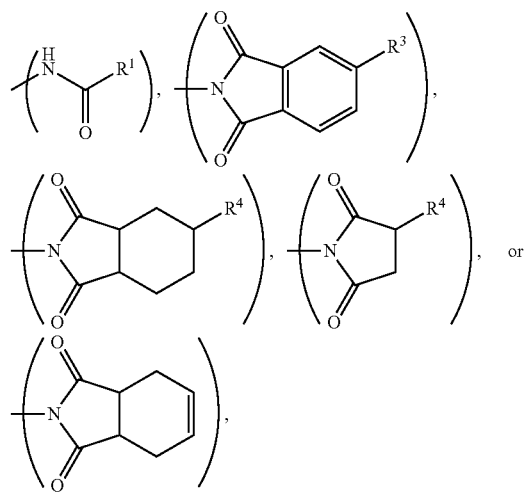

$R^1$ is an isopropyl or cyclohexyl, $R^3$ is H, an alkyl, or an alkoxy, $R^4$ is H, or C1-8 alkyl group, Ar is

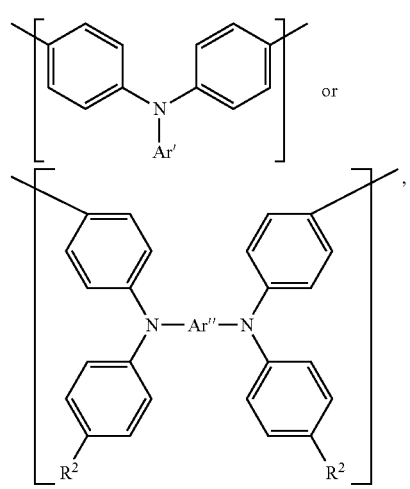

Ar' is

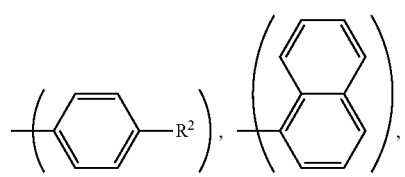

-continued

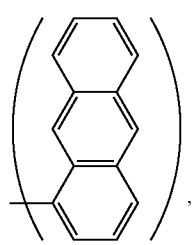,

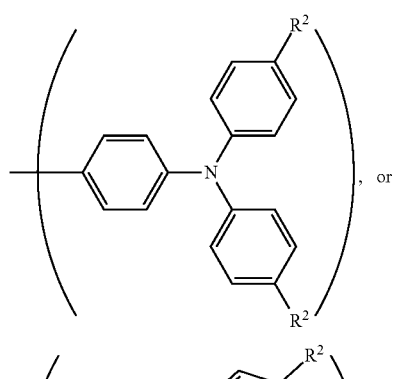, or

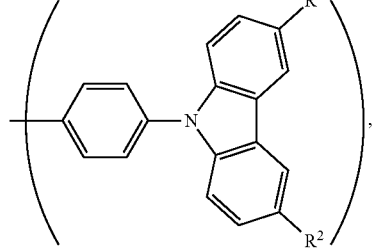

Ar″ is

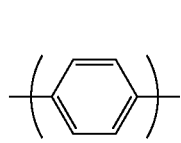 or 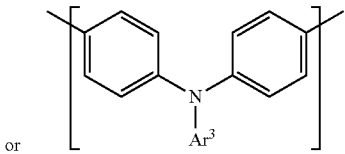,

Ar³ is

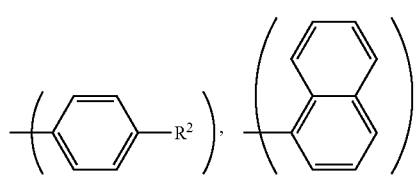,

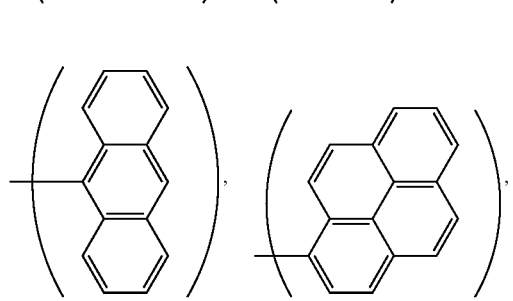

-continued

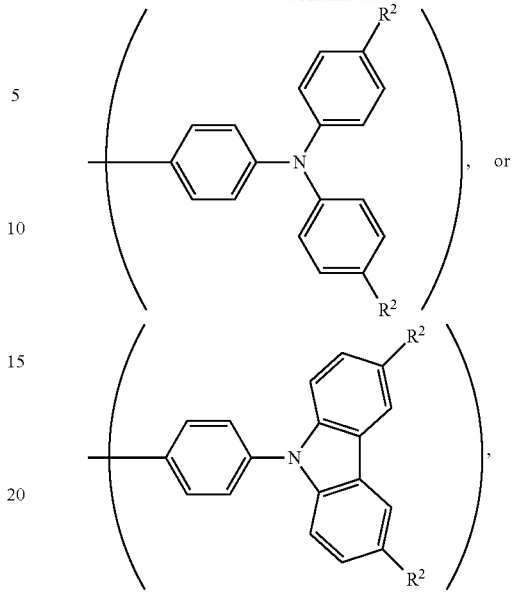, or

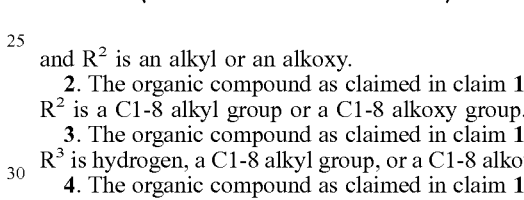, and $R^2$ is an alkyl or an alkoxy.

2. The organic compound as claimed in claim 1, wherein $R^2$ is a C1-8 alkyl group or a C1-8 alkoxy group.

3. The organic compound as claimed in claim 1, wherein $R^3$ is hydrogen, a C1-8 alkyl group, or a C1-8 alkoxy group.

4. The organic compound as claimed in claim 1, wherein the compound is represented by the following formula:

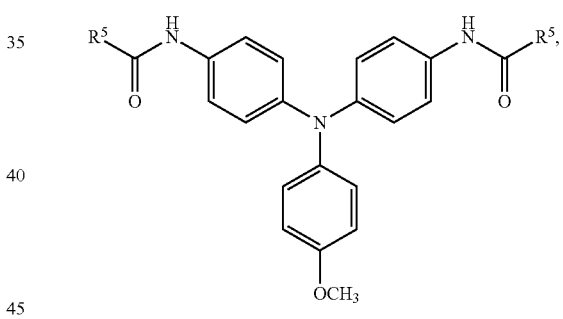

wherein $R^5$ is isopropyl or cyclohexyl.

5. The organic compound as claimed in claim 1, wherein the compound is represented by the following formula:

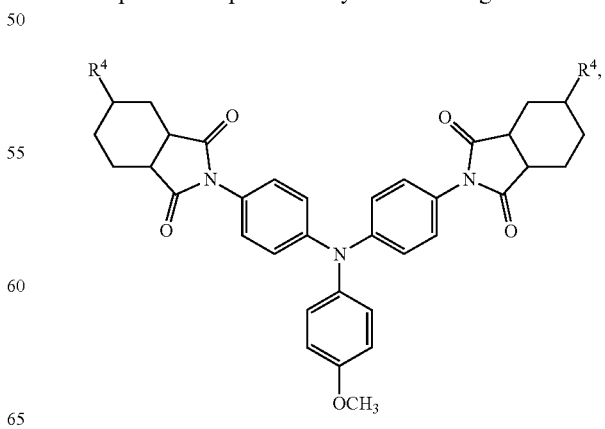

wherein $R^4$ is a C1-8 alkyl group.

6. The organic compound as claimed in claim 1, wherein the compound is represented by the following formula:

[chemical structure: tetraarylbenzene-1,4-diamine with two N-aryl amide substituents (R⁶-C(=O)NH-) and two 4-methoxyphenyl groups]

wherein R⁶ is isopropyl or cyclohexyl.

7. The organic compound as claimed in claim 1, wherein the compound is represented by the following formula:

[chemical structure: analogous diamine with two cyclohexane-fused phthalimide groups bearing R⁴ substituents, and two 4-methoxyphenyl groups]

wherein R⁴ is a C1-8 alkyl group.

8. A light modulating composition, comprising:
 a first oxidizable compound, wherein the first oxidizable compound is as claimed in claim 1;
 a reducible compound;
 an electrolyte; and
 a solvent.

9. The light modulating composition as claimed in claim 8, wherein the electrolyte is an organic ammonium salt or an inorganic lithium salt.

10. The light modulating composition as claimed in claim 8, wherein the oxidizable compound and the electrolyte have a mole ratio of 1:1 to 1:20, and the reducible compound and the electrolyte have a mole ratio of 1:1 to 1:20.

11. The light modulating composition as claimed in claim 8, wherein the concentration of the electrolyte is between 0.01M and 1.5M.

12. The light modulating composition as claimed in claim 8, wherein the reducible compound is selected from the group consisting of

[chemical structures: 1,4-naphthoquinone; 9,10-anthraquinone; and 4,4'-bipyridinium (viologen) salt with BF₄⁻ counterions and R⁷ substituents], and wherein R⁷ is a C1-C10 alkyl group.

13. The light modulating composition as claimed in claim 9, further comprising a second oxidizable compound selected from the group consisting of

[chemical structures: diphenylamine (R⁸), phenoxazine (R⁸), carbazole (R⁸), phenothiazine (R⁸), and dihydrophenazine (R⁸, R⁸)], and wherein R⁸ is H or an alkyl.

14. A light modulating device, comprising:
 a pair of electrodes, comprising:
  a first transparent substrate with a first transparent conductive layer on a surface of the transparent substrate; and
  a second transparent substrate with a second transparent conductive layer on a surface of the transparent substrate, disposed by arranging the first transparent conductive layer and the second transparent conductive layer to face each other;
 an isolating unit, inserted between the first and second transparent conductive layers to form a cell; and
 a light modulating composition filled in the cell,
 wherein the light modulating composition comprises:
  a first oxidizable compound, wherein the first oxidizable compound is as claimed in claim 1;
  a reducible compound;
  an electrolyte; and
  a solvent.

15. The light modulating device as claimed in claim 14, wherein the oxidizable compound is represented by the following formula:

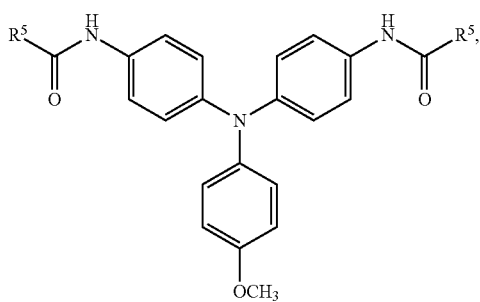

wherein R⁵ is an isopropyl or cyclohexyl.

16. The light modulating device as claimed in claim 14, wherein the oxidizable compound is represented by the following formula:

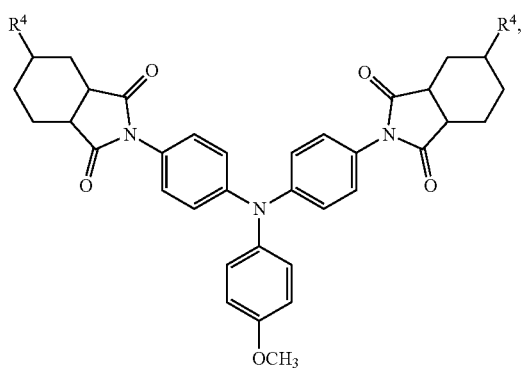

wherein R⁴ is a C1-8 alkyl group.

17. The light modulating device as claimed in claim 14, wherein the oxidizable compound is represented by the following formula:

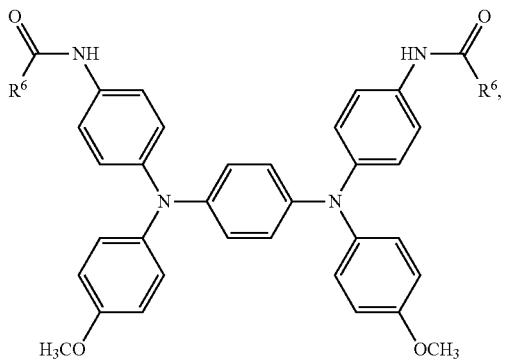

wherein R⁶ is an isopropyl or cyclohexyl.

18. The light modulating device as claimed in claim 14, wherein the oxidizable compound is represented by the following formula:

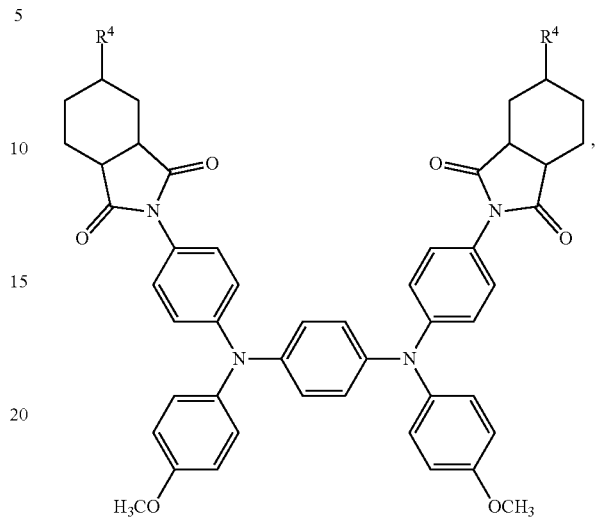

wherein R⁴ is a C1-8 alkyl group.

19. The light modulating device as claimed in claim 14, further comprising a second oxidizable compound, wherein the second oxidizable compound is selected from the group consisting of

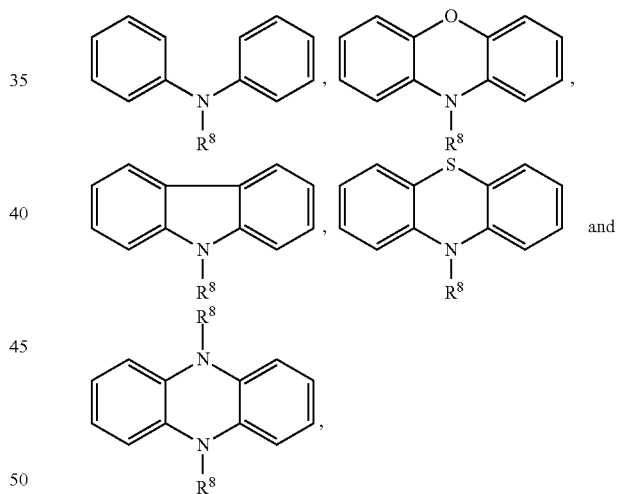

and wherein R⁵ is H or an alkyl.

20. The light modulating device as claimed in claim 14, wherein the distance from the first transparent conductive layer to the second transparent conductive layer is between 10 μm to 200 μm.

* * * * *